United States Patent
Askem et al.

(10) Patent No.: US 11,771,820 B2
(45) Date of Patent: Oct. 3, 2023

(54) NEGATIVE PRESSURE WOUND THERAPY APPARATUS FOR POST BREAST SURGERY WOUNDS

(71) Applicant: Smith & Nephew PLC, Watford (GB)

(72) Inventors: Ben Alan Askem, Brough (GB); John Philip Gowans, Hessle (GB); Stephanie Jane Noble, Hull (GB)

(73) Assignee: Smith & Nephew PLC, Watford (GB)

( * ) Notice: Subject to any disclaimer, the term of this patent is extended or adjusted under 35 U.S.C. 154(b) by 1059 days.

(21) Appl. No.: 16/081,398

(22) PCT Filed: Feb. 24, 2017

(86) PCT No.: PCT/EP2017/054369
§ 371 (c)(1),
(2) Date: Aug. 30, 2018

(87) PCT Pub. No.: WO2017/148824
PCT Pub. Date: Sep. 8, 2017

(65) Prior Publication Data
US 2019/0290499 A1  Sep. 26, 2019

Related U.S. Application Data

(60) Provisional application No. 62/380,907, filed on Aug. 29, 2016, provisional application No. 62/304,079, (Continued)

(51) Int. Cl.
*A61F 13/14* (2006.01)
*A61M 1/00* (2006.01)

(52) U.S. Cl.
CPC ............ *A61M 1/915* (2021.05); *A61F 13/145* (2013.01); *A61M 1/913* (2021.05); *A61M 1/985* (2021.05);
(Continued)

(58) Field of Classification Search
CPC ......... A61F 13/145; A61M 1/90; A61M 1/86; A61M 2205/7518; A61M 2210/1007
(Continued)

(56) References Cited

U.S. PATENT DOCUMENTS 3,929,135 A   12/1975   Thompson
3,972,328 A    8/1976   Chen
(Continued)

FOREIGN PATENT DOCUMENTS

CN   202822419 U   3/2013
CN   204670041 U   9/2015
(Continued)

OTHER PUBLICATIONS

Advantec MFS, Inc., "Membrane Filters" (catalog), retrieved from http://www.advantecmfs.com/catalog/filt/membrane.pdf, on Jan. 29, 2016, Copyright 2001-2011, 17 pages.
(Continued)

*Primary Examiner* — Andrew J Mensh
(74) *Attorney, Agent, or Firm* — Knobbe, Martens, Olson & Bear, LLP

(57) ABSTRACT

Disclosed embodiments relate to apparatuses and methods for wound treatment. In certain embodiments, a negative pressure wound therapy apparatus includes one or more wound dressings configured to be used to treat surgical wounds including post-breast surgery wounds. In some embodiments, a single negative pressure source can be used with one or more wound dressing to treat one or more wounds.

7 Claims, 14 Drawing Sheets

Related U.S. Application Data filed on Mar. 4, 2016, provisional application No. 62/304,010, filed on Mar. 4, 2016.

(52) U.S. Cl.
CPC .............. *A61M 2205/7518* (2013.01); *A61M 2210/1007* (2013.01)

(58) Field of Classification Search
USPC ........................................................ 604/319
See application file for complete search history.

(56) References Cited

U.S. PATENT DOCUMENTS

| | | | |
|---|---|---|---|
| 4,029,598 A | 6/1977 | Neisius et al. | |
| 4,728,499 A | 3/1988 | Fehder | |
| 4,813,942 A | 3/1989 | Alvarez | |
| 5,000,172 A | 3/1991 | Ward | |
| 5,056,510 A | 10/1991 | Gilman | |
| 5,106,629 A | 4/1992 | Cartmell et al. | |
| 5,181,905 A | 1/1993 | Flam | |
| 5,238,732 A | 8/1993 | Krishnan | |
| 5,447,492 A | 9/1995 | Cartmell et al. | |
| 5,549,584 A | 8/1996 | Gross | |
| 5,605,165 A | 2/1997 | Sessions et al. | |
| 5,707,499 A | 1/1998 | Joshi et al. | |
| 5,759,570 A | 6/1998 | Arnold | |
| 5,852,126 A | 12/1998 | Barnard et al. | |
| 5,960,795 A * | 10/1999 | Schultz ................. | A61F 13/023 128/888 |
| 6,008,429 A | 12/1999 | Ritger | |
| 6,071,267 A | 6/2000 | Zamierowski | |
| 6,345,623 B1 | 2/2002 | Heaton et al. | |
| 6,458,109 B1 | 10/2002 | Henley et al. | |
| 6,626,891 B2 | 9/2003 | Ohmstede | |
| 6,685,681 B2 | 2/2004 | Lockwood et al. | |
| 6,752,794 B2 | 6/2004 | Lockwood et al. | |
| 6,936,037 B2 | 8/2005 | Bubb et al. | |
| 6,951,553 B2 | 10/2005 | Bubb et al. | |
| 6,979,324 B2 | 12/2005 | Bybordi et al. | |
| 7,004,915 B2 | 2/2006 | Boynton et al. | |
| 7,070,584 B2 | 7/2006 | Johnson et al. | |
| 7,108,683 B2 | 9/2006 | Zamierowski | |
| 7,216,651 B2 | 5/2007 | Argenta et al. | |
| 7,338,482 B2 | 3/2008 | Lockwood et al. | |
| 7,361,184 B2 | 4/2008 | Joshi | |
| 7,381,859 B2 | 6/2008 | Hunt et al. | |
| 7,485,112 B2 | 2/2009 | Karpowicz et al. | |
| 7,569,742 B2 | 8/2009 | Haggstrom et al. | |
| 7,605,298 B2 | 10/2009 | Bechert et al. | |
| 7,615,036 B2 | 11/2009 | Joshi et al. | |
| 7,622,629 B2 | 11/2009 | Aali | |
| 7,625,362 B2 | 12/2009 | Boehringer et al. | |
| 7,699,823 B2 | 4/2010 | Haggstrom et al. | |
| 7,700,819 B2 | 4/2010 | Ambrosio et al. | |
| 7,708,724 B2 | 5/2010 | Weston | |
| 7,718,249 B2 | 5/2010 | Russell et al. | |
| 7,722,582 B2 | 5/2010 | Lina et al. | |
| 7,749,531 B2 | 7/2010 | Booher | |
| 7,759,537 B2 | 7/2010 | Bishop et al. | |
| 7,759,539 B2 | 7/2010 | Shaw et al. | |
| 7,775,998 B2 | 8/2010 | Riesinger | |
| 7,779,625 B2 | 8/2010 | Joshi et al. | |
| 7,846,141 B2 | 12/2010 | Weston | |
| 7,910,791 B2 | 3/2011 | Coffey | |
| 7,922,703 B2 | 4/2011 | Riesinger | |
| 7,945,302 B2 | 5/2011 | McAdams | |
| 7,959,624 B2 | 6/2011 | Riesinger | |
| 7,964,766 B2 | 6/2011 | Blott et al. | |
| 7,976,519 B2 | 7/2011 | Bubb et al. | |
| 8,021,347 B2 | 9/2011 | Vitaris et al. | |
| 8,034,037 B2 | 10/2011 | Adams et al. | |
| 8,062,272 B2 | 11/2011 | Weston | |
| 8,062,331 B2 | 11/2011 | Zamierowski | |
| 8,152,785 B2 | 4/2012 | Vitaris | |
| 8,162,907 B2 | 4/2012 | Heagle | |
| 8,235,972 B2 | 8/2012 | Adahan | |
| 8,241,261 B2 | 8/2012 | Randolph et al. | |
| 8,372,049 B2 | 2/2013 | Jaeb et al. | |
| 8,372,050 B2 | 2/2013 | Jaeb et al. | |
| 8,425,478 B2 | 4/2013 | Olson | |
| 8,444,611 B2 | 5/2013 | Wilkes et al. | |
| 8,513,481 B2 | 8/2013 | Gergely et al. | |
| 8,540,688 B2 | 9/2013 | Eckstein et al. | |
| 8,545,466 B2 | 10/2013 | Andresen et al. | |
| 8,568,386 B2 | 10/2013 | Malhi | |
| 8,641,691 B2 | 2/2014 | Fink et al. | |
| 8,663,198 B2 | 3/2014 | Buan et al. | |
| 8,682,442 B2 | 3/2014 | McAdams | |
| 8,715,256 B2 | 5/2014 | Greener | |
| 8,751,180 B2 | 6/2014 | Lull et al. | |
| 8,764,732 B2 | 7/2014 | Hartwell | |
| 8,795,247 B2 | 8/2014 | Bennett et al. | |
| 8,795,800 B2 | 8/2014 | Evans | |
| 8,808,274 B2 | 8/2014 | Hartwell | |
| 8,834,451 B2 | 9/2014 | Blott et al. | |
| 8,834,452 B2 | 9/2014 | Hudspeth et al. | |
| 8,974,429 B2 | 3/2015 | Gordon et al. | |
| 9,012,714 B2 | 4/2015 | Fleischmann | |
| 9,061,095 B2 | 6/2015 | Adie et al. | |
| 9,067,003 B2 | 6/2015 | Buan et al. | |
| 9,127,665 B2 | 9/2015 | Locke et al. | |
| 9,199,012 B2 | 12/2015 | Vitaris et al. | |
| 9,283,118 B2 | 3/2016 | Locke et al. | |
| 9,421,309 B2 | 8/2016 | Robinson et al. | |
| 9,427,505 B2 | 8/2016 | Askem et al. | |
| 9,526,439 B2 | 12/2016 | Connelly et al. | |
| 9,681,993 B2 | 6/2017 | Wu et al. | |
| 9,682,179 B2 | 6/2017 | May | |
| 9,829,471 B2 | 11/2017 | Hammond et al. | |
| 10,046,096 B2 | 8/2018 | Askem et al. | |
| 10,058,642 B2 | 8/2018 | Weston | |
| 10,155,070 B2 | 12/2018 | Childress et al. | |
| 10,328,188 B2 | 6/2019 | Deutsch et al. | |
| 2002/0062114 A1 | 5/2002 | Murai et al. | |
| 2003/0125646 A1 | 7/2003 | Whitlock | |
| 2004/0015115 A1 | 1/2004 | Sinyagin | |
| 2004/0057855 A1 | 3/2004 | Gerlach et al. | |
| 2005/0004501 A1 * | 1/2005 | Lorenzo ................... | A61F 5/03 602/75 |
| 2005/0209574 A1 | 9/2005 | Boehringer et al. | |
| 2005/0222527 A1 | 10/2005 | Miller et al. | |
| 2005/0288691 A1 | 12/2005 | Leiboff | |
| 2006/0009744 A1 | 1/2006 | Erdman et al. | |
| 2007/0016152 A1 | 1/2007 | Karpowicz et al. | |
| 2007/0040454 A1 | 2/2007 | Freudenberger et al. | |
| 2007/0055209 A1 | 3/2007 | Patel et al. | |
| 2007/0219497 A1 | 9/2007 | Johnson et al. | |
| 2007/0219512 A1 | 9/2007 | Heaton et al. | |
| 2007/0225663 A1 | 9/2007 | Watt et al. | |
| 2007/0255194 A1 | 11/2007 | Gudnason et al. | |
| 2008/0031748 A1 | 2/2008 | Ihle et al. | |
| 2008/0132821 A1 | 6/2008 | Propp et al. | |
| 2008/0200096 A1 * | 8/2008 | Thornton .............. | A61F 13/141 450/37 |
| 2008/0306456 A1 | 12/2008 | Riesinger | |
| 2009/0125004 A1 | 5/2009 | Shen et al. | |
| 2009/0157024 A1 | 6/2009 | Song | |
| 2009/0234306 A1 | 9/2009 | Vitaris | |
| 2009/0293887 A1 | 12/2009 | Wilkes et al. | |
| 2009/0299251 A1 | 12/2009 | Buan | |
| 2009/0299306 A1 | 12/2009 | Buan | |
| 2010/0125258 A1 | 5/2010 | Coulthard et al. | |
| 2010/0259406 A1 | 10/2010 | Caso et al. | |
| 2010/0268111 A1 | 10/2010 | Drinan et al. | |
| 2010/0318052 A1 | 12/2010 | Ha et al. | |
| 2011/0004172 A1 | 1/2011 | Eckstein et al. | |
| 2011/0224631 A1 | 9/2011 | Simmons et al. | |
| 2011/0313339 A1 * | 12/2011 | Vitaris ................... | A61M 27/00 602/54 |
| 2012/0051945 A1 | 3/2012 | Orndorff et al. | |
| 2012/0123358 A1 | 5/2012 | Hall et al. | |
| 2012/0136325 A1 | 5/2012 | Allen et al. | |
| 2012/0190956 A1 | 7/2012 | Connolly | |

(56) References Cited

U.S. PATENT DOCUMENTS

| | | | |
|---|---|---|---|
| 2012/0209226 A1 | 8/2012 | Simmons et al. | |
| 2013/0066285 A1 | 3/2013 | Locke et al. | |
| 2013/0066289 A1 | 3/2013 | Song et al. | |
| 2013/0090616 A1 | 4/2013 | Neubauer | |
| 2013/0144227 A1 | 6/2013 | Locke et al. | |
| 2013/0150813 A1 | 6/2013 | Gordon et al. | |
| 2013/0165878 A1 | 6/2013 | Heagle | |
| 2013/0296762 A1 | 11/2013 | Toth | |
| 2013/0302545 A1 | 11/2013 | Schnelker et al. | |
| 2014/0114268 A1 | 4/2014 | Auguste et al. | |
| 2014/0200533 A1 | 7/2014 | Whyte et al. | |
| 2014/0228789 A1* | 8/2014 | Wilkes | A61F 13/00029 604/319 |
| 2014/0316359 A1 | 10/2014 | Collinson et al. | |
| 2014/0332088 A1 | 11/2014 | Senesh | |
| 2014/0350494 A1* | 11/2014 | Hartwell | A61F 13/00068 604/319 |
| 2015/0032035 A1 | 1/2015 | Banwell et al. | |
| 2015/0119831 A1 | 4/2015 | Robinson et al. | |
| 2015/0119832 A1 | 4/2015 | Locke | |
| 2015/0119833 A1 | 4/2015 | Coulthard et al. | |
| 2015/0231021 A1* | 8/2015 | Smith | A61M 1/0003 601/7 |
| 2016/0000611 A1 | 1/2016 | Niederauer et al. | |
| 2016/0045377 A1 | 2/2016 | Robinson et al. | |
| 2016/0081580 A1 | 3/2016 | Bergelin et al. | |
| 2016/0101282 A1 | 4/2016 | Bergelin et al. | |
| 2016/0120706 A1 | 5/2016 | Collinson et al. | |
| 2016/0287763 A1 | 10/2016 | Simmons et al. | |
| 2016/0298620 A1 | 10/2016 | Cordoba et al. | |
| 2017/0028111 A1 | 2/2017 | Tumey et al. | |
| 2017/0156658 A1 | 6/2017 | Maharbiz et al. | |
| 2017/0368239 A1 | 12/2017 | Askem et al. | |
| 2018/0055359 A1 | 3/2018 | Shamim et al. | |
| 2018/0133378 A1 | 5/2018 | Askem et al. | |
| 2018/0168916 A1 | 6/2018 | Kelch et al. | |
| 2018/0318476 A1 | 11/2018 | Askem et al. | |
| 2020/0121833 A9 | 4/2020 | Askem et al. | |

FOREIGN PATENT DOCUMENTS

| | | |
|---|---|---|
| DE | 3443101 A1 | 5/1986 |
| EP | 0340018 A2 | 11/1989 |
| EP | 1476217 B1 | 3/2008 |
| EP | 1955887 A2 | 8/2008 |
| EP | 2462908 A1 | 6/2012 |
| EP | 3037115 A1 | 6/2016 |
| EP | 3628289 B1 | 11/2021 |
| FR | 1163907 A | 10/1958 |
| GB | 1255395 A | 12/1971 |
| GB | 2307180 B | 6/2000 |
| GB | 2468905 A | 9/2010 |
| JP | 2014237992 A | 12/2014 |
| JP | 2016118204 A | 6/2016 |
| WO | WO-8300742 A1 | 3/1983 |
| WO | WO-9216245 A1 | 10/1992 |
| WO | WO-9605873 A1 | 2/1996 |
| WO | WO-2004077387 A1 | 9/2004 |
| WO | WO-2005046760 A1 | 5/2005 |
| WO | WO-2005105180 A1 | 11/2005 |
| WO | WO-2007013049 A1 | 2/2007 |
| WO | WO-2007113597 A2 | 10/2007 |
| WO | WO-2008039223 A1 | 4/2008 |
| WO | WO-2009124100 A1 | 10/2009 |
| WO | WO-2009147402 A2 | 12/2009 |
| WO | WO-2009158128 A2 | 12/2009 |
| WO | WO-2010142959 A2 | 12/2010 |
| WO | WO-2011135285 A1 | 11/2011 |
| WO | WO-2011135286 A1 | 11/2011 |
| WO | WO-2011135287 A1 | 11/2011 |
| WO | WO-2011144888 A1 | 11/2011 |
| WO | WO 2012/021553 | 2/2012 |
| WO | WO-2012131237 A1 | 10/2012 |
| WO | WO-2012143665 A1 | 10/2012 |
| WO | WO-2013010907 A1 | 1/2013 |
| WO | WO-2013064852 A1 | 5/2013 |
| WO | WO-2013078095 A2 | 5/2013 |
| WO | WO-2013083800 A1 | 6/2013 |
| WO | WO-2013090810 A1 | 6/2013 |
| WO | WO-2013149078 A1 | 10/2013 |
| WO | WO-2014008348 A2 | 1/2014 |
| WO | WO-2014016759 A1 | 1/2014 |
| WO | WO-2014020440 A1 | 2/2014 |
| WO | WO-2014020443 A2 | 2/2014 |
| WO | WO-2014108476 A1 | 7/2014 |
| WO | WO 2014/140606 | 9/2014 |
| WO | WO 2014/140608 | 9/2014 |
| WO | WO-2015022334 A1 | 2/2015 |
| WO | WO-2015022340 A1 | 2/2015 |
| WO | WO-2015031216 A1 | 3/2015 |
| WO | WO-2015168720 A1 | 11/2015 |
| WO | WO-2016018448 A1 | 2/2016 |
| WO | WO-2016109041 A1 | 7/2016 |
| WO | WO-2016174048 A1 | 11/2016 |
| WO | WO 2017/148824 | 9/2017 |
| WO | WO-2017197357 A1 | 11/2017 |
| WO | WO-2018041854 A1 | 3/2018 |

OTHER PUBLICATIONS

Hersle K., et al., "Uses of Dextranomer Absorbent Pads After Cryosurgery of Cutaneous Malignancies," The Journal of Dermatologic Surgery and Oncology, vol. 8, Jan. 1982, pp. 35-37.

International Preliminary Report on Patentability for Application No. PCT/EP2017/054369, dated Sep. 13, 2018, 12 pages.

KCI Licensing Inc, "Prevena™ Incision Management System—Clinician Guide—Instructions for Use," 390061 Rev D, Jan. 2010, 10 pages.

KCI Licensing Inc, "Prevena™ Incision Management System—Clinician Guide—Instructions for Use," 390153-WEB Rev B, Jan. 2010, 12 pages.

KCI Licensing, "Prevena™ Incision Management System—Patient Guide", 390064 Rev D, Jan. 2010, 4 pages.

KCI Licensing, "Prevena™ Incision Management System—Patient Guide," 390152-WEB C, Jan. 2011, 6 pages.

KCI Licensing, Prevena™ Incision Management System, Jun. 22, 2010, in 2 pages.

Kendall ULTEC Hydrocolloid Dressing (4x4"), Product Ordering Page, web page downloaded on Jul. 13, 2014, 1 page.

Protz K., "Modern Wound Dressings Support the Healing Process," Wound care: Indications and Application, Geriatrie Journal, Apr. 2005, pp. 3333-3339 (17 pages with English translation).

Smith & Nephew, Allevyn Gentle Border Multisite, Jun. 2011, 2 pages.

Smith & Nephew, "PICO Single Use Negative Pressure Wound Therapy System," Spiral Booklet, Mar. 2011, 7 pages.

Smith and Nephew Inc., "Allevyn Wound Dressings Pamphlet," 2008, 2 pages.

Smith and Nephew Medical Ltd., "Reach for the Right Dressing. Reach for Allevyn," Allevyn Educational Booklet, Apr. 2014, 2 pages.

Technology Watch, May 1989, 1 page.

International Search Report and Written Opinion, re PCT Application No. PCT/EP2017/054369, dated Aug. 24, 2017.

KCI, "V.A.C. Therapy Clinical guidelines: A reference source for clinicians", KCI Ltd., Nov. 2005 (New, revised edition), in 24 pages.

Smith & Nephew, "Clinical Cases—PICO Bilateral Breast Reduction Study", Aug. 2014, in 8 pages.

U.S. Appl. No. 16/120,056, System for Providing Wound Dressing Port and Associated Wound Dressing, filed Aug. 31, 2018.

* cited by examiner

NEGATIVE PRESSURE WOUND THERAPY APPARATUS FOR POST BREAST SURGERY WOUNDS

CROSS-REFERENCE TO RELATED APPLICATIONS

This application is a U.S. national stage application of International Patent Application No. PCT/EP2017/054369, filed on Feb. 24, 2017, which claims priority to U.S. Provisional Application No. 62/304,010, filed Mar. 4, 2016, U.S. Provisional Application No. 62/304,079, filed Mar. 4, 2016, and U.S. Provisional Application No. 62/380,907, filed Aug. 29, 2016, the entireties of which are hereby incorporated by reference.

BACKGROUND

Technical Field

Embodiments described herein relate to apparatuses, systems, and methods the treatment of wounds, for example using dressings in combination with negative pressure wound therapy, particularly for post-breast surgery wounds.

Description of the Related Art

The treatment of open or chronic wounds that are too large to spontaneously close or otherwise fail to heal by means of applying negative pressure to the site of the wound is well known in the art. Negative pressure wound therapy (NPWT) systems currently known in the art commonly involve placing a cover that is impermeable or semi-permeable to fluids over the wound, using various means to seal the cover to the tissue of the patient surrounding the wound, and connecting a source of negative pressure (such as a vacuum pump) to the cover in a manner so that negative pressure is created and maintained under the cover. It is believed that such negative pressures promote wound healing by facilitating the formation of granulation tissue at the wound site and assisting the body's normal inflammatory process while simultaneously removing excess fluid, which may contain adverse cytokines and/or bacteria. However, further improvements in NPWT are needed to fully realize the benefits of treatment.

Many different types of wound dressings are known for aiding in NPWT systems. These different types of wound dressings include many different types of materials and layers, for example, gauze, pads, foam pads or multi-layer wound dressings. One example of a multi-layer wound dressing is the PICO dressing, available from Smith & Nephew, which includes a superabsorbent layer beneath a backing layer to provide a canister-less system for treating a wound with NPWT. The wound dressing may be sealed to a suction port providing connection to a length of tubing, which may be used to pump fluid out of the dressing and/or to transmit negative pressure from a pump to the wound dressing.

Certain wounds have shapes that are difficult to treat with negative pressure wound therapy. It may be desirable, in some situations, to provide a wound dressing shaped to fit a specific region of the body or wound type so that it is shaped and contoured around that area allowing full coverage and even application of negative pressure throughout the treatment area. For example, it can be difficult to apply a standard wound dressing to post-breast surgery wounds.

SUMMARY

Embodiments of the present disclosure relate to apparatuses and methods for wound treatment. Some of the wound treatment apparatuses described herein comprise a negative pressure source or a pump system for providing negative pressure to a wound. Wound treatment apparatuses may also comprise wound dressings that may be used in combination with the negative pressure sources and pump assemblies described herein. In some embodiments, one or more dressings can be used to treat one or more surgical wounds including post-breast surgery wounds.

In some aspects, a negative pressure wound therapy apparatus is provided, comprising: a wound dressing comprising an elongate portion having a longitudinal axis and a bridging portion, wherein the bridging portion comprises a first end and a second end, wherein the bridging portion extends away from a middle portion of the elongate portion at a substantially right angle from the longitudinal axis at the first end of the bridging portion, the wound dressing comprising within both the elongate portion and the bridging portion: a wound contact layer configured to be positioned in contact with a wound; an absorbent layer and/or transmission layer over the wound contact layer; and a cover layer configured to cover and form a seal over the wound contact layer and the absorbent layer and/or transmission layer, wherein the cover layer comprises an aperture at a second end of the bridging portion; and a fluidic connector positioned over the aperture in the cover layer at the second end of the bridging portion.

The apparatus of the preceding paragraph may also include any combination of the following features described in this paragraph, among others described herein. In some embodiments, the elongate portion is rectangular having a length parallel to the longitudinal axis and a width perpendicular to the longitudinal axis, wherein the length is greater than the width. In some embodiments, the elongate portion comprises a first lobe on a first side of the bridging portion and a second lobe on a second side of the bridging portion. In some embodiments, the elongate portion comprises a bra shape. In some embodiments, the absorbent layer/and or transmission layer is a continuous layer between the bridging portion and the elongate portion. In some embodiments, the bridging portion is rectangular. In some embodiments, the wound contact layer is a single sheet of material across the elongate portion and the bridging portion. In some embodiments, the cover layer is a single sheet of material across the elongate portion and the bridging portion. In some embodiments, elongate portion is sized and configured to cover one or more post-surgical breast wounds, with the bridging portion being located between the breasts.

In another aspect, a negative pressure wound therapy apparatus is provided, comprising: a wound dressing comprising an elongate portion comprising two lobes and a bridging portion, wherein the elongate portion comprises a longitudinal axis and the bridging portion is positioned in a middle portion of the elongate portion along the longitudinal axis, a first lobe on a first side of the bridging portion and a second lobe on a second side of the bridging portion, the wound dressing comprising within both the elongate portion and the bridging portion: a wound contact layer configured to be positioned in contact with a wound; an absorbent layer and/or transmission layer over the wound contact layer; and a cover layer configured to cover and form a seal over the wound contact layer and the absorbent layer and/or transmission layer, wherein the cover layer comprises an aperture in the bridging portion; and a fluidic connector positioned over the aperture in the cover layer at the bridging portion.

The apparatus of the preceding paragraph may also include any combination of the following features described in this paragraph, among others described herein. In some embodiments, the first and second lobes comprise a substantially triangular shape having edges and corners. In some embodiments, the first and second lobes comprise a long edge shared between the first triangular shaped lobe and the second triangular shaped lobe. In some embodiments, the first and second lobes comprise a substantially oval or circular shape. In some embodiments, the absorbent layer/and or transmission layer is a continuous layer between the bridging portion and the elongate portion. In some embodiments, the bridging portion is rectangular and extends perpendicularly away from the elongate portion. In some embodiments, the wound contact layer is a single sheet of material across the elongate portion and the bridging portion. In some embodiments, the cover layer is a single sheet of material across the elongate portion and the bridging portion. In some embodiments, the one or more lobes are sized and configured to cover one or more post-surgical breast wounds, with the bridging portion being located between the breasts.

In another aspect, a negative pressure wound therapy apparatus is provided, comprising: a wound dressing comprising an elongate portion having a longitudinal axis and a bridging portion, wherein the bridging portion comprises a first end and a second end, wherein the bridging portion extends away from a middle portion of the elongate portion at a substantially right angle from the longitudinal axis at the first end of the bridging portion, the wound dressing comprising within both the elongate portion and the bridging portion: a wound contact layer configured to be positioned in contact with a wound; an absorbent layer and/or transmission layer over the wound contact layer; and a cover layer configured to cover and form a seal over the wound contact layer and the absorbent layer and/or transmission layer, wherein the cover layer comprises an aperture at a second end of the bridging portion; and a fluidic connector positioned over the aperture in the cover layer at the second end of the bridging portion; wherein the elongate portion and the bridging portion are sized and configured to cover one or more post-surgical breast wounds, with the elongate portion and the bridging portion sized and configured to be located on a single breast.

The apparatus of the preceding paragraph may also include any combination of the following features described in this paragraph, among others described herein. In some embodiments, the elongate portion is rectangular having a length parallel to the longitudinal axis and a width perpendicular to the longitudinal axis, wherein the length is greater than the width. In some embodiments, the absorbent layer/ and or transmission layer is a continuous layer between the bridging portion and the elongate portion. In some embodiments, the bridging portion is rectangular. In some embodiments, the wound contact layer is a single sheet of material across the elongate portion and the bridging portion. In some embodiments, the cover layer is a single sheet of material across the elongate portion and the bridging portion. In some embodiments, the wound dressing is a first wound dressing and the fluid connector is a first fluid connector, and further comprises a second wound dressing comprising an elongate portion having a longitudinal axis and a bridging portion, wherein the bridging portion comprises a first end and a second end, wherein the bridging portion extends away from a middle portion of the elongate portion at a substantially right angle from the longitudinal axis at the first end of the bridging portion, the second wound dressing comprising within both the elongate portion and the bridging portion: a wound contact layer configured to be positioned in contact with a wound; an absorbent layer and/or transmission layer over the wound contact layer; and a cover layer configured to cover and form a seal over the wound contact layer and the absorbent layer and/or transmission layer, wherein the cover layer comprises an aperture at a second end of the bridging portion; and a second fluidic connector positioned over the aperture in the cover layer of the second wound dressing at the second end of the bridging portion of the second wound dressing; wherein the elongate portion and the bridging portion of the second wound dressing are sized and configured to cover one or more post-surgical breast wounds, with the elongate portion and the bridging portion of the second wound dressing sized and configured to be located on a different breast than that of the first wound dressing. In some embodiments, the first fluidic connector and the second fluidic connector are configured to be connected to a single negative pressure source via a Y-shaped connector.

In another aspect, a negative pressure wound therapy apparatus is provided, comprising: a wound dressing comprising a triangular shape, the wound dressing having three edges and three corners, the wound dressing comprising: a wound contact layer configured to be positioned in contact with a wound; an absorbent layer and/or transmission layer over the wound contact layer; and a cover layer configured to cover and form a seal over the wound contact layer and the absorbent layer and/or transmission layer, wherein the cover layer comprises an aperture positioned near an edge of the triangular shaped dressing; and a fluidic connector positioned over the aperture in the cover layer near the edge of the triangular shaped dressing.

The apparatus of the preceding paragraph may also include any combination of the following features described in this paragraph, among others described herein. In some embodiments, the wound dressing is sized and configured to cover one or more post-surgical breast wounds, wherein the dressing is configured to cover a single breast. In some embodiments, the wound dressing is a first wound dressing and the fluidic connector is a first fluid connector, and further comprises a second wound dressing comprising a triangular shape, the second wound dressing having three edges and three corners, the second wound dressing comprising: a wound contact layer configured to be positioned in contact with a wound; an absorbent layer and/or transmission layer over the wound contact layer; and a cover layer configured to cover and form a seal over the wound contact layer and the absorbent layer and/or transmission layer, wherein the cover layer comprises an aperture positioned near an edge of the triangular shaped dressing; and a second fluidic connector positioned over the aperture in the cover layer of the second wound dressing near the edge of the second triangular shaped dressing. In some embodiments, the second wound dressing is sized and configured to cover one or more post-surgical breast wounds, wherein the second dressing is configured to cover a different breast than that of the first wound dressing. In some embodiments, the first fluidic connector and the second fluidic connector are configured to be connected to a single negative pressure source via a Y-shaped connector.

In other aspects, a negative pressure wound therapy apparatus is provided which comprises a first wound dressing and a second wound dressing, each wound dressing sized and configured to be located on different breasts. In some embodiments, the apparatus comprises a Y-shaped connector configured to connect to the first and second wound dressings, for example via first and second fluidic connectors positioned in fluid communication with the first and second wound dressings, respectively. A single negative pressure source may be provided to connect to the Y-shaped connector to provide negative pressure simultaneously to both the first and second wound dressings.

In some embodiments, each of the first and second wound dressings may comprise an elongate portion having a longitudinal axis and a bridging portion, wherein the bridging portion comprises a first end and a second end, wherein the bridging portion extends away from a middle portion of the elongate portion at a substantially right angle from the longitudinal axis at the first end of the bridging portion. Each of the first and second wound dressings may comprise within the elongate portion and the bridging portion: a wound contact layer configured to be positioned in contact with a wound; an absorbent layer and/or transmission layer over the wound contact layer; and a cover layer configured to cover and form a seal over the wound contact layer and the absorbent layer and/or transmission layer, wherein the cover layer comprises an aperture at a second end of the bridging portion. First and second fluidic connectors may be positioned over the aperture in the cover layer of the first and second wound dressings, respectively, at the second end of the bridging portion. The elongate portion and the bridging portion of each of the first and second wound dressings may be sized and configured to cover one or more post-surgical breast wounds of different breasts.

Any of the features, components, or details of any of the arrangements or embodiments disclosed in this application, including without limitation any of the pump embodiments and any of the negative pressure wound therapy embodiments disclosed below, are interchangeably combinable with any other features, components, or details of any of the arrangements or embodiments disclosed herein to form new arrangements and embodiments.

DETAILED DESCRIPTION

Figure 1A:
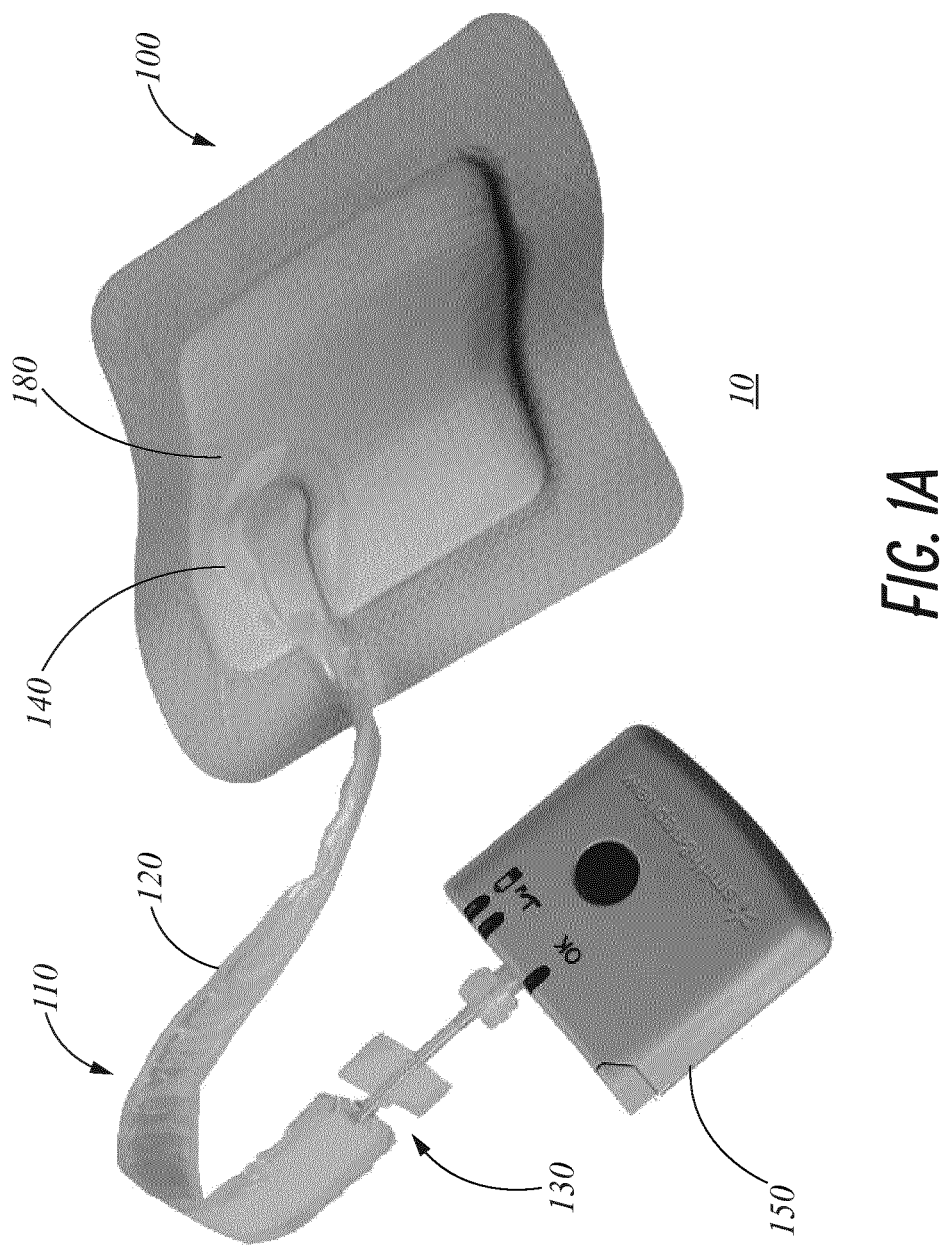
FIG. 1A illustrates an embodiment of a negative pressure wound treatment system employing a flexible fluidic connector and a wound dressing capable of absorbing and storing wound exudate.

Embodiments disclosed herein relate to apparatuses and methods of treating a wound with reduced pressure, including a source of negative pressure and wound dressing components and apparatuses. The apparatuses and components comprising the wound overlay and packing materials, if any, are sometimes collectively referred to herein as dressings.

Preferred embodiments disclosed herein relate to wound therapy for a human or animal body. Therefore, any reference to a wound herein can refer to a wound on a human or animal body, and any reference to a body herein can refer to a human or animal body. The term "wound" as used herein, in addition to having its broad ordinary meaning, includes any body part of a patient that may be treated using negative pressure. It is to be understood that the term wound is to be broadly construed and encompasses open and closed wounds in which skin is torn, cut or punctured or where trauma causes a contusion, or any other superficial or other conditions or imperfections on the skin of a patient or otherwise that benefit from reduced pressure treatment. A wound is thus broadly defined as any damaged region of tissue where fluid may or may not be produced. Examples of such wounds include, but are not limited to, abdominal wounds or other large or incisional wounds, either as a result of surgery, trauma, sterniotomies, fasciotomies, or other conditions, dehisced wounds, acute wounds, chronic wounds, subacute and dehisced wounds, traumatic wounds, flaps and skin grafts, lacerations, abrasions, contusions, burns, diabetic ulcers, pressure ulcers, stoma, surgical wounds, trauma and venous ulcers or the like.

Treatment of such wounds can be performed using negative pressure wound therapy, wherein a reduced or negative pressure can be applied to the wound to facilitate and promote healing of the wound. It will also be appreciated that the wound dressing and methods as disclosed herein may be applied to other parts of the body, and are not necessarily limited to treatment of wounds.

It will be understood that embodiments of the present disclosure are generally applicable to use in topical negative pressure ("TNP") therapy systems. Briefly, negative pressure wound therapy assists in the closure and healing of many forms of "hard to heal" wounds by reducing tissue oedema; encouraging blood flow and granular tissue formation; removing excess exudate and may reduce bacterial load (and thus infection risk). In addition, the therapy allows for less disturbance of a wound leading to more rapid healing. TNP therapy systems may also assist on the healing of surgically closed wounds by removing fluid and by helping to stabilize the tissue in the apposed position of closure. A further beneficial use of TNP therapy can be found in grafts and flaps where removal of excess fluid is important and close proximity of the graft to tissue is required in order to ensure tissue viability.

As is used herein, reduced or negative pressure levels, such as −X mmHg, represent pressure levels relative to normal ambient atmospheric pressure, which can correspond to 760 mmHg (or 1 atm, 29.93 inHg, 101.325 kPa, 14.696 psi, etc.). Accordingly, a negative pressure value of −X mmHg reflects absolute pressure that is X mmHg below 760 mmHg or, in other words, an absolute pressure of (760−X) mmHg. In addition, negative pressure that is "less" or "smaller" than X mmHg corresponds to pressure that is closer to atmospheric pressure (e.g., −40 mmHg is less than −60 mmHg). Negative pressure that is "more" or "greater" than −X mmHg corresponds to pressure that is further from atmospheric pressure (e.g., −80 mmHg is more than −60 mmHg). In some embodiments, local ambient atmospheric pressure is used as a reference point, and such local atmospheric pressure may not necessarily be, for example, 760 mmHg.

The negative pressure range for some embodiments of the present disclosure can be approximately −80 mmHg, or between about −20 mmHg and −200 mmHg. Note that these pressures are relative to normal ambient atmospheric pressure, which can be 760 mmHg. Thus, −200 mmHg would be about 560 mmHg in practical terms. In some embodiments, the pressure range can be between about −40 mmHg and −150 mmHg. Alternatively a pressure range of up to −75 mmHg, up to −80 mmHg or over −80 mmHg can be used. Also in other embodiments a pressure range of below −75 mmHg can be used. Alternatively, a pressure range of over approximately −100 mmHg, or even −150 mmHg, can be supplied by the negative pressure apparatus.

In some embodiments of wound closure devices described herein, increased wound contraction can lead to increased tissue expansion in the surrounding wound tissue. This effect may be increased by varying the force applied to the tissue, for example by varying the negative pressure applied to the wound over time, possibly in conjunction with increased tensile forces applied to the wound via embodiments of the wound closure devices. In some embodiments, negative pressure may be varied over time for example using a sinusoidal wave, square wave, and/or in synchronization with one or more patient physiological indices (e.g., heartbeat). Examples of such applications where additional disclosure relating to the preceding may be found include U.S. Pat. No. 8,235,955, titled "Wound treatment apparatus and method," issued on Aug. 7, 2012; and U.S. Pat. No. 7,753,894, titled "Wound cleansing apparatus with stress," issued Jul. 13, 2010. The disclosures of both of these patents are hereby incorporated by reference in their entirety.

Embodiments of the wound dressings, wound dressing components, wound treatment apparatuses and methods described herein may also be used in combination or in addition to those described in International Application No. PCT/IB2013/001469, filed May 22, 2013, published as WO 2013/175306 A2 on Nov. 28, 2013, titled "APPARATUSES AND METHODS FOR NEGATIVE PRESSURE WOUND THERAPY," U.S. patent application Ser. No. 14/418,874, filed Jan. 30, 2015, published as US 2015/0190286 A1 on Jul. 9, 2015, titled "WOUND DRESSING AND METHOD OF TREATMENT," the disclosures of which are hereby incorporated by reference in their entireties. Embodiments of the wound dressings, wound treatment apparatuses and methods described herein may also be used in combination or in addition to those described in U.S. patent application Ser. No. 13/092,042, filed Apr. 21 2011, published as US2011/0282309, titled "WOUND DRESSING AND METHOD OF USE," and U.S. patent application Ser. No. 14/715,527, filed May 18, 2015, titled "FLUIDIC CONNECTOR FOR NEGATIVE PRESSURE WOUND THERAPY," the disclosures of which are hereby incorporated by reference in its entirety, including further details relating to embodiments of wound dressings, the wound dressing components and principles, and the materials used for the wound dressings.

Additionally, some embodiments related to TNP wound treatment comprising a wound dressing in combination with a pump and/or associated electronics described herein may also be used in combination or in addition to those described in PCT Application No. PCT/EP2016/059329, filed Apr. 26, 2016, entitled "REDUCED PRESSURE APPARATUS AND METHODS".

Figure 1B:
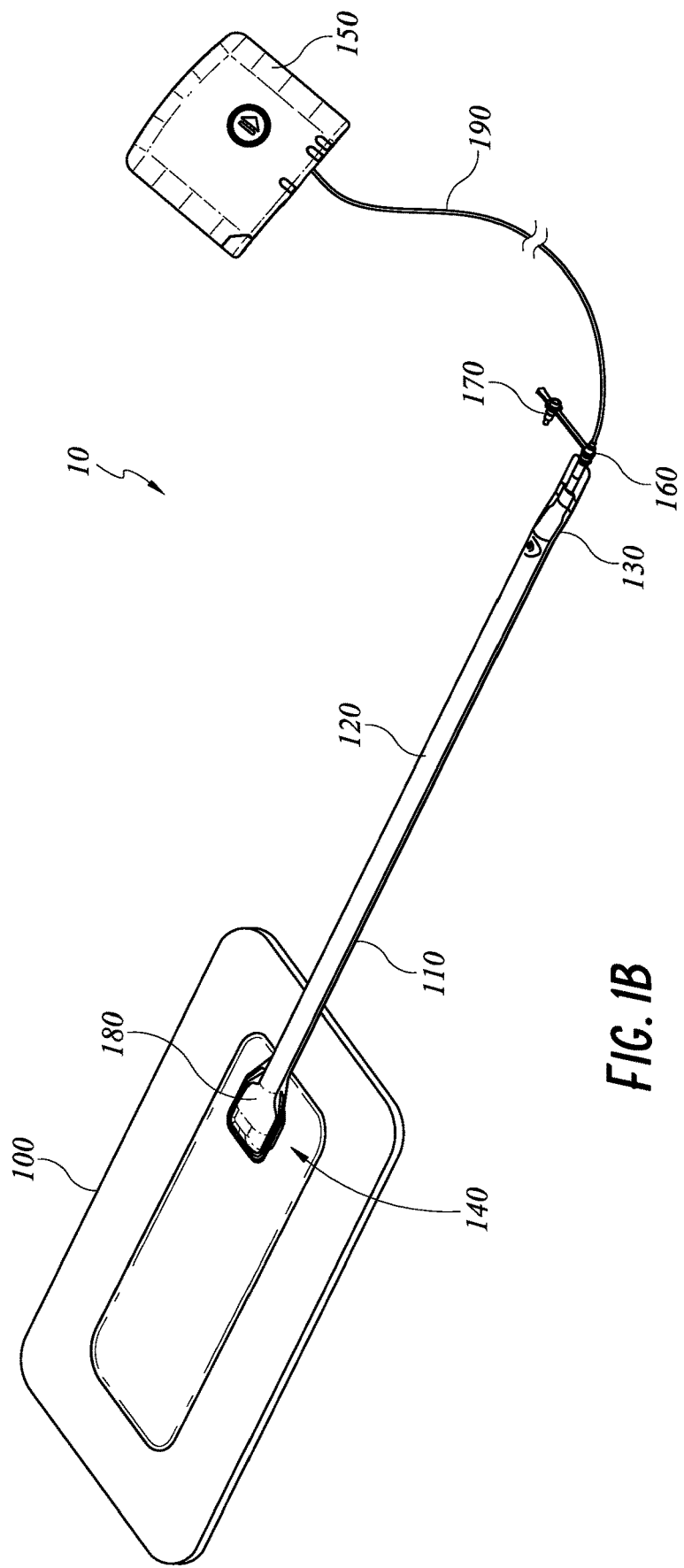
FIG. 1B illustrates an embodiment of a negative pressure wound treatment system employing a flexible fluidic connector and a wound dressing capable of absorbing and storing wound exudate.

FIGS. 1A-B illustrate embodiments of a negative pressure wound treatment system 10 employing a wound dressing 100 in conjunction with a fluidic connector 110. Here, the fluidic connector 110 may comprise an elongate conduit, more preferably a bridge 120 having a proximal end 130 and a distal end 140, and an applicator 180 at the distal end 140 of the bridge 120. An optional coupling 160 is preferably disposed at the proximal end 130 of the bridge 120. A cap 170 may be provided with the system (and can in some cases, as illustrated, be attached to the coupling 160). The cap 170 can be useful in preventing fluids from leaking out of the proximal end 130. The system 10 may include a source of negative pressure such as a pump or negative pressure unit 150 capable of supplying negative pressure. The pump may comprise a canister or other container for the storage of wound exudates and other fluids that may be removed from the wound. A canister or container may also be provided separate from the pump. In some embodiments, such as illustrated in FIGS. 1A-1B, the pump 150 can be a canisterless pump such as the PICO™ pump, as sold by Smith & Nephew. The pump 150 may be connected to the coupling 160 via a tube 190, or the pump 150 may be connected directly to the coupling 160 or directly to the bridge 120. In use, the dressing 100 is placed over a suitably-prepared wound, which may in some cases be filled with a wound packing material such as foam or gauze. The applicator 180 of the fluidic connector 110 has a sealing surface that is placed over an aperture in the dressing 100 and is sealed to the top surface of the dressing 100. In other embodiments, the fluidic connector 110 that is positioned over the aperture in the dressing can also include a fluidic connector 110 that has a portion of the fluidic connector 110 positioned on the underside of the top layer or cover layer of the dressing. In some embodiments, the fluidic connector can include a flange that can be attached to the underside or top surface of the cover layer. Either before, during, or after connection of the fluidic connector 110 to the dressing 100, the pump 150 is connected via the tube 190 to the coupling 160, or is connected directly to the coupling 160 or to the bridge 120. The pump is then activated, thereby supplying negative pressure to the wound. Application of negative pressure may be applied until a desired level of healing of the wound is achieved.

Figure 2A:
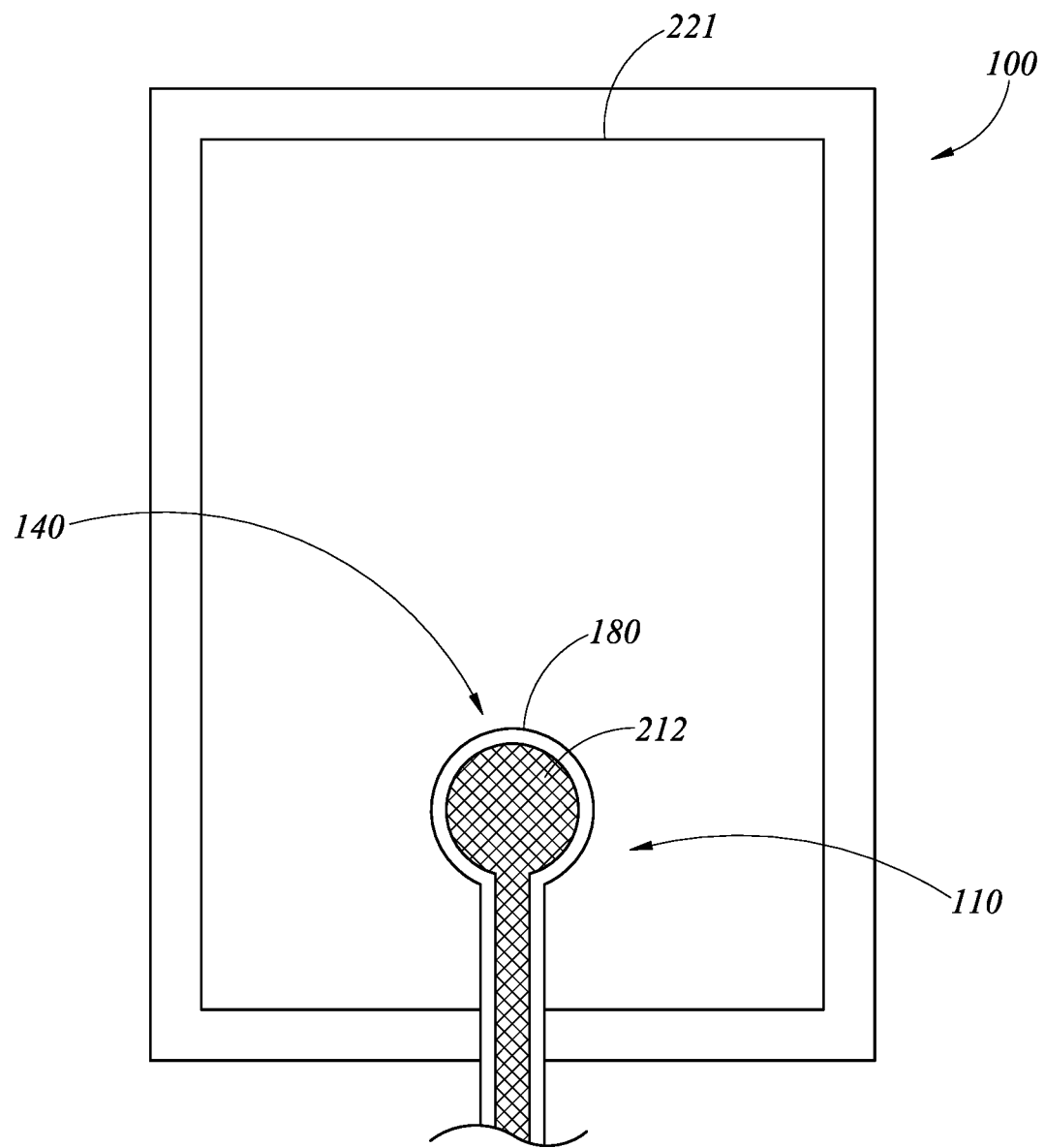
FIG. 2A illustrates an embodiment of a negative pressure wound treatment system employing a flexible fluidic connector and a wound dressing capable of absorbing and storing wound exudate.

As shown in FIG. 2A, the fluidic connector 110 preferably comprises an enlarged distal end, or head 140 that is in fluidic communication with the dressing 100 as will be described in further detail below. In one embodiment, the enlarged distal end has a round or circular shape. The head 140 is illustrated here as being positioned near an edge of the dressing 100, but may also be positioned at any location on the dressing. For example, some embodiments may provide for a centrally or off-centered location not on or near an edge or corner of the dressing 100. In some embodiments, the dressing 10 may comprise two or more fluidic connectors 110, each comprising one or more heads 140, in fluidic communication therewith. In a preferred embodiment, the head 140 may measure 30*mm* along its widest edge. The head 140 forms at least in part the applicator 180, described above, that is configured to seal against a top surface of the wound dressing.

Figure 2B:
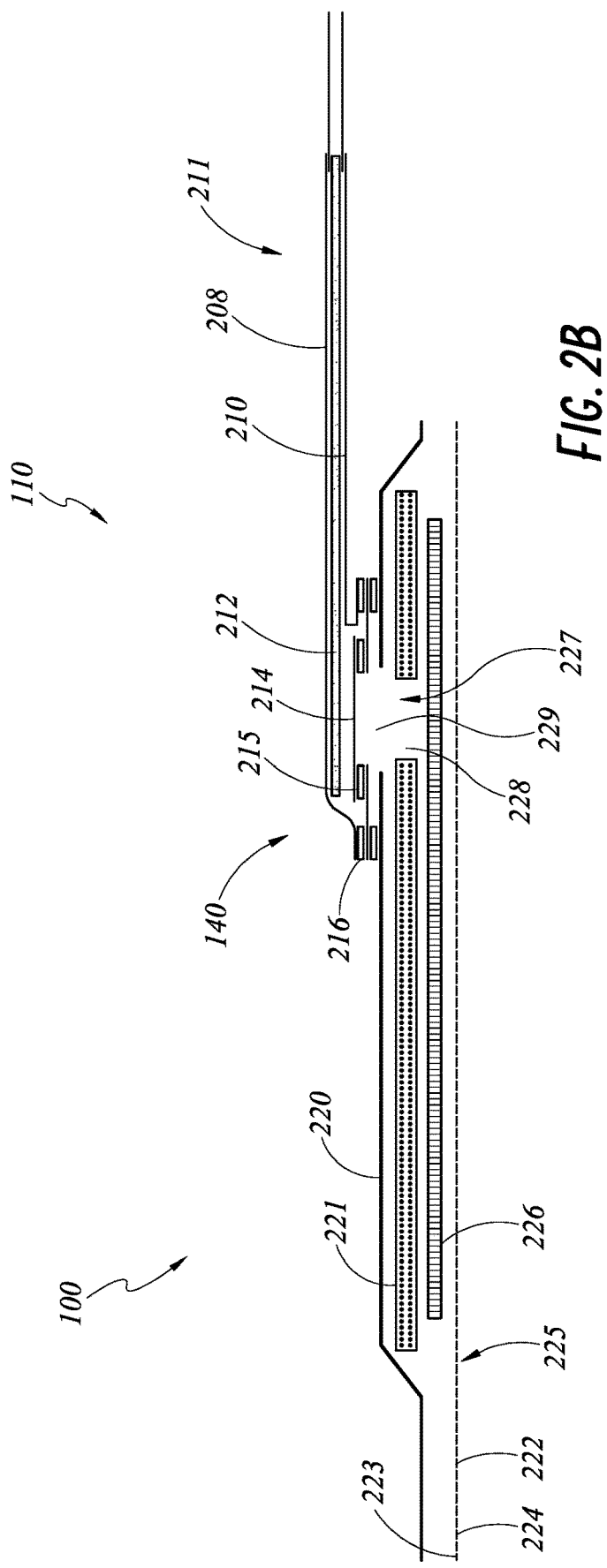
FIG. 2B illustrates a cross section of an embodiment of a fluidic connector connected to a wound dressing.

FIG. 2B illustrates a cross-section through a wound dressing 100 similar to the wound dressing 10 as shown in FIG. 1B and described in International Patent Publication WO2013175306 A2, which is incorporated by reference in its entirety, along with fluidic connector 110. The wound dressing 100, which can alternatively be any wound dressing embodiment disclosed herein or any combination of features of any number of wound dressing embodiments disclosed herein, can be located over a wound site to be treated. The dressing 100 may be placed as to form a sealed cavity over the wound site. In a preferred embodiment, the dressing 100 comprises a top or cover layer, or backing layer 220 attached to an optional wound contact layer 222, both of which are described in greater detail below. These two layers 220, 222 are preferably joined or sealed together so as to define an interior space or chamber. This interior space or chamber may comprise additional structures that may be adapted to distribute or transmit negative pressure, store wound exudate and other fluids removed from the wound, and other functions which will be explained in greater detail below. Examples of such structures, described below, include a transmission layer 226 and an absorbent layer 221.

As used herein the upper layer, top layer, or layer above refers to a layer furthest from the surface of the skin or wound while the dressing is in use and positioned over the wound. Accordingly, the lower surface, lower layer, bottom layer, or layer below refers to the layer that is closest to the surface of the skin or wound while the dressing is in use and positioned over the wound.

As illustrated in FIG. 2B, the wound contact layer 222 can be a polyurethane layer or polyethylene layer or other flexible layer which is perforated, for example via a hot pin process, laser ablation process, ultrasound process or in some other way or otherwise made permeable to liquid and gas. The wound contact layer 222 has a lower surface 224 and an upper surface 223. The perforations 225 preferably comprise through holes in the wound contact layer 222 which enable fluid to flow through the layer 222. The wound contact layer 222 helps prevent tissue ingrowth into the other material of the wound dressing. Preferably, the perforations are small enough to meet this requirement while still allowing fluid to flow therethrough. For example, perforations formed as slits or holes having a size ranging from 0.025 mm to 1.2 mm are considered small enough to help prevent tissue ingrowth into the wound dressing while allowing wound exudate to flow into the dressing. In some configurations, the wound contact layer 222 may help maintain the integrity of the entire dressing 100 while also creating an air tight seal around the absorbent pad in order to maintain negative pressure at the wound.

Some embodiments of the wound contact layer 222 may also act as a carrier for an optional lower and upper adhesive layer (not shown). For example, a lower pressure sensitive adhesive may be provided on the lower surface 224 of the wound dressing 100 whilst an upper pressure sensitive adhesive layer may be provided on the upper surface 223 of the wound contact layer. The pressure sensitive adhesive, which may be a silicone, hot melt, hydrocolloid or acrylic based adhesive or other such adhesives, may be formed on both sides or optionally on a selected one or none of the sides of the wound contact layer. When a lower pressure sensitive adhesive layer is utilized may be helpful to adhere the wound dressing 100 to the skin around a wound site. In some embodiments, the wound contact layer may comprise perforated polyurethane film. The lower surface of the film may be provided with a silicone pressure sensitive adhesive and the upper surface may be provided with an acrylic pressure sensitive adhesive, which may help the dressing maintain its integrity. In some embodiments, a polyurethane film layer may be provided with an adhesive layer on both its upper surface and lower surface, and all three layers may be perforated together.

A layer 226 of porous material can be located above the wound contact layer 222. This porous layer, or transmission layer, 226 allows transmission of fluid including liquid and gas away from a wound site into upper layers of the wound dressing. In particular, the transmission layer 226 preferably ensures that an open air channel can be maintained to communicate negative pressure over the wound area even when the absorbent layer has absorbed substantial amounts of exudates. The layer 226 should preferably remain open under the typical pressures that will be applied during negative pressure wound therapy as described above, so that the whole wound site sees an equalized negative pressure. The layer 226 may be formed of a material having a three dimensional structure. For example, a knitted or woven spacer fabric (for example Baltex 7970 weft knitted polyester) or a non-woven fabric could be used.

In some embodiments, the transmission layer 226 comprises a 3D polyester spacer fabric layer including a top layer (that is to say, a layer distal from the wound-bed in use) which is a 84/144 textured polyester, and a bottom layer (that is to say, a layer which lies proximate to the wound bed in use) which is a 10 denier flat polyester and a third layer formed sandwiched between these two layers which is a region defined by a knitted polyester viscose, cellulose or the like mono filament fiber. Other materials and other linear mass densities of fiber could of course be used.

Whilst reference is made throughout this disclosure to a monofilament fiber it will be appreciated that a multistrand alternative could of course be utilized. The top spacer fabric thus has more filaments in a yarn used to form it than the number of filaments making up the yarn used to form the bottom spacer fabric layer.

This differential between filament counts in the spaced apart layers helps control moisture flow across the transmission layer. Particularly, by having a filament count greater in the top layer, that is to say, the top layer is made from a yarn having more filaments than the yarn used in the bottom layer, liquid tends to be wicked along the top layer more than the bottom layer. In use, this differential tends to draw liquid away from the wound bed and into a central region of the dressing where the absorbent layer 221 helps lock the liquid away or itself wicks the liquid onwards towards the cover layer where it can be transpired.

Preferably, to improve the liquid flow across the transmission layer 226 (that is to say perpendicular to the channel region formed between the top and bottom spacer layers, the 3D fabric may be treated with a dry cleaning agent (such as, but not limited to, Perchloro Ethylene) to help remove any manufacturing products such as mineral oils, fats and/or waxes used previously which might interfere with the hydrophilic capabilities of the transmission layer. In some embodiments, an additional manufacturing step can subsequently be carried in which the 3D spacer fabric is washed in a hydrophilic agent (such as, but not limited to, Feran Ice 30 g/l available from the Rudolph Group). This process step helps ensure that the surface tension on the materials is so low that liquid such as water can enter the fabric as soon as it contacts the 3D knit fabric. This also aids in controlling the flow of the liquid insult component of any exudates.

A layer 221 of absorbent material is provided above the transmission layer 226. The absorbent material, which comprise a foam or non-woven natural or synthetic material, and which may optionally comprise a super-absorbent material, forms a reservoir for fluid, particularly liquid, removed from the wound site. In some embodiments, the layer 10 may also aid in drawing fluids towards the backing layer 220.

The material of the absorbent layer 221 may also prevent liquid collected in the wound dressing 100 from flowing freely within the dressing, and preferably acts so as to contain any liquid collected within the dressing. The absorbent layer 221 also helps distribute fluid throughout the layer via a wicking action so that fluid is drawn from the wound site and stored throughout the absorbent layer. This helps prevent agglomeration in areas of the absorbent layer. The capacity of the absorbent material must be sufficient to manage the exudates flow rate of a wound when negative pressure is applied. Since in use the absorbent layer experiences negative pressures the material of the absorbent layer is chosen to absorb liquid under such circumstances. A number of materials exist that are able to absorb liquid when under negative pressure, for example superabsorber material. The absorbent layer 221 may typically be manufactured from ALLEVYN™ foam, Freudenberg 114-224-4 and/or Chem-Posite™11C-450. In some embodiments, the absorbent layer 221 may comprise a composite comprising super-absorbent powder, fibrous material such as cellulose, and bonding fibers. In a preferred embodiment, the composite is an airlaid, thermally-bonded composite.

In some embodiments, the absorbent layer 221 is a layer of non-woven cellulose fibers having super-absorbent material in the form of dry particles dispersed throughout. Use of the cellulose fibers introduces fast wicking elements which help quickly and evenly distribute liquid taken up by the dressing. The juxtaposition of multiple strand-like fibers leads to strong capillary action in the fibrous pad which helps distribute liquid. In this way, the super-absorbent material is efficiently supplied with liquid. The wicking action also assists in bringing liquid into contact with the upper cover layer to aid increase transpiration rates of the dressing.

An aperture, hole, or orifice 227 is preferably provided in the backing layer 220 to allow a negative pressure to be applied to the dressing 100. The fluidic connector 110 is preferably attached or sealed to the top of the backing layer 220 over the orifice 227 made into the dressing 100, and communicates negative pressure through the orifice 227. A length of tubing may be coupled at a first end to the fluidic connector 110 and at a second end to a pump unit (not shown) to allow fluids to be pumped out of the dressing. Where the fluidic connector is adhered to the top layer of the wound dressing, a length of tubing may be coupled at a first end of the fluidic connector such that the tubing, or conduit, extends away from the fluidic connector parallel or substantially to the top surface of the dressing. The fluidic connector 110 may be adhered and sealed to the backing layer 220 using an adhesive such as an acrylic, cyanoacrylate, epoxy, UV curable or hot melt adhesive. The fluidic connector 110 may be formed from a soft polymer, for example a polyethylene, a polyvinyl chloride, a silicone or polyurethane having a hardness of 30 to 90 on the Shore A scale. In some embodiments, the fluidic connector 110 may be made from a soft or conformable material.

Preferably the absorbent layer 221 includes at least one through hole 228 located so as to underlie the fluidic connector 110. The through hole 228 may in some embodiments be the same size as the opening 227 in the backing layer, or may be bigger or smaller. As illustrated in FIG. 2B a single through hole can be used to produce an opening underlying the fluidic connector 110. It will be appreciated that multiple openings could alternatively be utilized. Additionally, should more than one port be utilized according to certain embodiments of the present disclosure one or multiple openings may be made in the absorbent layer and the obscuring layer in registration with each respective fluidic connector. Although not essential to certain embodiments of the present disclosure the use of through holes in the super-absorbent layer may provide a fluid flow pathway which remains unblocked in particular when the absorbent layer is near saturation.

The aperture or through-hole 228 is preferably provided in the absorbent layer 221 beneath the orifice 227 such that the orifice is connected directly to the transmission layer 226 as illustrated in FIG. 2B. This allows the negative pressure applied to the fluidic connector 110 to be communicated to the transmission layer 226 without passing through the absorbent layer 221. This ensures that the negative pressure applied to the wound site is not inhibited by the absorbent layer as it absorbs wound exudates. In other embodiments, no aperture may be provided in the absorbent layer 221, or alternatively a plurality of apertures underlying the orifice 227 may be provided. In further alternative embodiments, additional layers such as another transmission layer or an obscuring layer such as described in International Patent Publication WO2014020440, the entirety of which is hereby incorporated by reference, may be provided over the absorbent layer 221 and beneath the backing layer 220.

The backing layer 220 is preferably gas impermeable, but moisture vapor permeable, and can extend across the width of the wound dressing 100. The backing layer 220, which may for example be a polyurethane film (for example, Elastollan SP9109) having a pressure sensitive adhesive on one side, is impermeable to gas and this layer thus operates to cover the wound and to seal a wound cavity over which the wound dressing is placed. In this way an effective chamber is made between the backing layer 220 and a wound site where a negative pressure can be established. The backing layer 220 is preferably sealed to the wound contact layer 222 in a border region around the circumference of the dressing, ensuring that no air is drawn in through the border area, for example via adhesive or welding techniques. The backing layer 220 protects the wound from external bacterial contamination (bacterial barrier) and allows liquid from wound exudates to be transferred through the layer and evaporated from the film outer surface. The backing layer 220 preferably comprises two layers; a polyurethane film and an adhesive pattern spread onto the film. The polyurethane film is preferably moisture vapor permeable and may be manufactured from a material that has an increased water transmission rate when wet. In some embodiments the moisture vapor permeability of the backing layer increases when the backing layer becomes wet. The moisture vapor permeability of the wet backing layer may be up to about ten times more than the moisture vapor permeability of the dry backing layer.

The absorbent layer 221 may be of a greater area than the transmission layer 226, such that the absorbent layer overlaps the edges of the transmission layer 226, thereby ensuring that the transmission layer does not contact the backing layer 220. This provides an outer channel of the absorbent layer 221 that is in direct contact with the wound contact layer 222, which aids more rapid absorption of exudates to the absorbent layer. Furthermore, this outer channel ensures that no liquid is able to pool around the circumference of the wound cavity, which may otherwise seep through the seal around the perimeter of the dressing leading to the formation of leaks. As illustrated in FIGS. 2A-2B, the absorbent layer 221 may define a smaller perimeter than that of the backing layer 220, such that a boundary or border region is defined between the edge of the absorbent layer 221 and the edge of the backing layer 220.

As shown in FIG. 2B, one embodiment of the wound dressing 100 comprises an aperture 228 in the absorbent layer 221 situated underneath the fluidic connector 110. In use, for example when negative pressure is applied to the dressing 100, a wound facing portion of the fluidic connector may thus come into contact with the transmission layer 226, which can thus aid in transmitting negative pressure to the wound site even when the absorbent layer 221 is filled with wound fluids. Some embodiments may have the backing layer 220 be at least partly adhered to the transmission layer 226. In some embodiments, the aperture 228 is at least 1-2 mm larger than the diameter of the wound facing portion of the fluidic connector 11, or the orifice 227.

In particular for embodiments with a single fluidic connector 110 and through hole, it may be preferable for the fluidic connector 110 and through hole to be located in an off-center position as illustrated in FIG. 2A. Such a location may permit the dressing 100 to be positioned onto a patient such that the fluidic connector 110 is raised in relation to the remainder of the dressing 100. So positioned, the fluidic connector 110 and the filter 214 may be less likely to come into contact with wound fluids that could prematurely occlude the filter 214 so as to impair the transmission of negative pressure to the wound site.

Turning now to the fluidic connector 110, preferred embodiments comprise a sealing surface 216, a bridge 211 (corresponding to bridge 120 in FIGS. 1A-1B) with a proximal end 130 and a distal end 140, and a filter 214. The sealing surface 216 preferably forms the applicator previously described that is sealed to the top surface of the wound dressing. In some embodiments a bottom layer of the fluidic connector 110 may comprise the sealing surface 216. The fluidic connector 110 may further comprise an upper surface vertically spaced from the sealing surface 216, which in some embodiments is defined by a separate upper layer of the fluidic connector. In other embodiments the upper surface and the lower surface may be formed from the same piece of material. In some embodiments the sealing surface 216 may comprise at least one aperture 229 therein to communicate with the wound dressing. In some embodiments the filter 214 may be positioned across the opening 229 in the sealing surface, and may span the entire opening 229. The sealing surface 216 may be configured for sealing the fluidic connector to the cover layer of the wound dressing, and may comprise an adhesive or weld. In some embodiments, the sealing surface 216 may be placed over an orifice in the cover layer with optional spacer elements 215 configured to create a gap between the filter 214 and the transmission layer 226. In other embodiments, the sealing surface 216 may be positioned over an orifice in the cover layer and an aperture in the absorbent layer 220, permitting the fluidic connector 110 to provide air flow through the transmission layer 226. In some embodiments, the bridge 211 may comprise a first fluid passage 212 in communication with a source of negative pressure, the first fluid passage 212 comprising a porous material, such as a 3D knitted material, which may be the same or different than the porous layer 226 described previously. The bridge 211 is preferably encapsulated by at least one flexible film layer 208, 210 having a proximal and distal end and configured to surround the first fluid passage 212, the distal end of the flexible film being connected the sealing surface 216. The filter 214 is configured to substantially prevent wound exudate from entering the bridge, and spacer elements 215 are configured to prevent the fluidic connector from contacting the transmission layer 226. These elements will be described in greater detail below.

Some embodiments may further comprise an optional second fluid passage positioned above the first fluid passage 212. For example, some embodiments may provide for an air leak may be disposed at the proximal end of the top layer that is configured to provide an air path into the first fluid passage 212 and dressing 100 similar to the suction adapter as described in U.S. Pat. No. 8,801,685, which is incorporated by reference herein in its entirety.

Preferably, the fluid passage 212 is constructed from a compliant material that is flexible and that also permits fluid to pass through it if the spacer is kinked or folded over. Suitable materials for the fluid passage 212 include without limitation foams, including open-cell foams such as polyethylene or polyurethane foam, meshes, 3D knitted fabrics, non-woven materials, and fluid channels. In some embodiments, the fluid passage 212 may be constructed from materials similar to those described above in relation to the transmission layer 226. Advantageously, such materials used in the fluid passage 212 not only permit greater patient comfort, but may also provide greater kink resistance, such that the fluid passage 212 is still able to transfer fluid from the wound toward the source of negative pressure while being kinked or bent.

In some embodiments, the fluid passage 212 may be comprised of a wicking fabric, for example a knitted or woven spacer fabric (such as a knitted polyester 3D fabric, Baltex 7970®, or Gehring 879®) or a nonwoven fabric. These materials selected are preferably suited to channeling wound exudate away from the wound and for transmitting negative pressure and/or vented air to the wound site, and may also confer a degree of kinking or occlusion resistance to the fluid passage 212. In some embodiments, the wicking fabric may have a three-dimensional structure, which in some cases may aid in wicking fluid or transmitting negative pressure. In certain embodiments, including wicking fabrics, these materials remain open and capable of communicating negative pressure to a wound area under the typical pressures used in negative pressure therapy, for example between 40 to 150 mmHg. In some embodiments, the wicking fabric may comprise several layers of material stacked or layered over each other, which may in some cases be useful in preventing the fluid passage 212 from collapsing under the application of negative pressure. In other embodiments, the wicking fabric used in the fluid passage 212 may be between 1.5 mm and 6 mm; more preferably, the wicking fabric may be between 3 mm and 6 mm thick, and may be comprised of either one or several individual layers of wicking fabric. In other embodiments, the fluid passage 212 may be between 1.2-3 mm thick, and preferably thicker than 1.5 mm. Some embodiments, for example a suction adapter used with a dressing which retains liquid such as wound exudate, may employ hydrophobic layers in the fluid passage 212, and only gases may travel through the fluid passage 212. Additionally, and as described previously, the materials used in the system are preferably conformable and soft, which may help to avoid pressure ulcers and other complications which may result from a wound treatment system being pressed against the skin of a patient.

Preferably, the filter element 214 is impermeable to liquids, but permeable to gases, and is provided to act as a liquid bather and to ensure that no liquids are able to escape from the wound dressing 100. The filter element 214 may also function as a bacterial bather. Typically the pore size is 0.2 μm. Suitable materials for the filter material of the filter element 214 include 0.2 micron Gore™ expanded PTFE from the MMT range, PALL Versapore™ 200R, and Donaldson™ TX6628. Larger pore sizes can also be used but these may require a secondary filter layer to ensure full bioburden containment. As wound fluid contains lipids it is preferable, though not essential, to use an oleophobic filter membrane for example 1.0 micron MMT-332 prior to 0.2 micron MMT-323. This prevents the lipids from blocking the hydrophobic filter. The filter element can be attached or sealed to the port and/or the cover film over the orifice. For example, the filter element 214 may be molded into the fluidic connector 110, or may be adhered to one or both of the top of the cover layer and bottom of the suction adapter 110 using an adhesive such as, but not limited to, a UV cured adhesive.

It will be understood that other types of material could be used for the filter element 214. More generally a microporous membrane can be used which is a thin, flat sheet of polymeric material, this contains billions of microscopic pores. Depending upon the membrane chosen these pores can range in size from 0.01 to more than 10 micrometers. Microporous membranes are available in both hydrophilic (water filtering) and hydrophobic (water repellent) forms. In some embodiments of the invention, filter element 214 comprises a support layer and an acrylic co-polymer membrane formed on the support layer. Preferably the wound dressing 100 according to certain embodiments of the present invention uses microporous hydrophobic membranes (MHMs). Numerous polymers may be employed to form MHMs. For example, the MHMs may be formed from one or more of PTFE, polypropylene, PVDF and acrylic copolymer. All of these optional polymers can be treated in order to obtain specific surface characteristics that can be both hydrophobic and oleophobic. As such these will repel liquids with low surface tensions such as multi-vitamin infusions, lipids, surfactants, oils and organic solvents.

MHMs block liquids whilst allowing air to flow through the membranes. They are also highly efficient air filters eliminating potentially infectious aerosols and particles. A single piece of MHM is well known as an option to replace mechanical valves or vents. Incorporation of MHMs can thus reduce product assembly costs improving profits and costs/benefit ratio to a patient.

The filter element 214 may also include an odor absorbent material, for example activated charcoal, carbon fiber cloth or Vitec Carbotec-RT Q2003073 foam, or the like. For example, an odor absorbent material may form a layer of the filter element 214 or may be sandwiched between microporous hydrophobic membranes within the filter element. The filter element 214 thus enables gas to be exhausted through the orifice. Liquid, particulates and pathogens however are contained in the dressing.

The wound dressing 100 may comprise spacer elements 215 in conjunction with the fluidic connector 110 and the filter 214. With the addition of such spacer elements 215 the fluidic connector 110 and filter 214 may be supported out of direct contact with the absorbent layer 220 and/or the transmission layer 226. The absorbent layer 220 may also act as an additional spacer element to keep the filter 214 from contacting the transmission layer 226. Accordingly, with such a configuration contact of the filter 214 with the transmission layer 226 and wound fluids during use may thus be minimized.

Similar to the embodiments of wound dressings described above, some wound dressings comprise a perforated wound contact layer with silicone adhesive on the skin-contact face and acrylic adhesive on the reverse. Above this bordered layer sits a transmission layer or a 3D spacer fabric pad. Above the transmission layer, sits an absorbent layer. The absorbent layer can include a superabsorbent non-woven (NW) pad. The absorbent layer can over-border the transmission layer by approximately 5 mm at the perimeter. The absorbent layer can have an aperture or through-hole toward one end. The aperture can be about 10 mm in diameter. Over the transmission layer and absorbent layer lies a backing layer. The backing layer can be a high moisture vapor transmission rate (MVTR) film, pattern coated with acrylic adhesive. The high MVTR film and wound contact layer encapsulate the transmission layer and absorbent layer, creating a perimeter border of approximately 20 mm. The backing layer can have a 10 mm aperture that overlies the aperture in the absorbent layer. Above the hole can be bonded a fluidic connector that comprises a liquid-impermeable, gas-permeable semi-permeable membrane (SPM) or filter that overlies the aforementioned apertures.

Figure 3A:
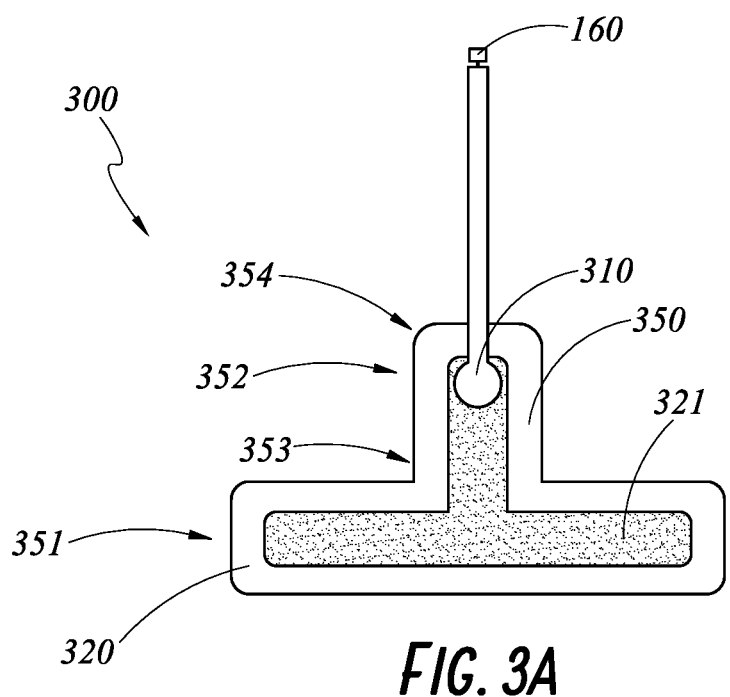
FIG. 3A illustrates an embodiment of a negative pressure wound treatment system employing a wound dressing with a T shape.
Figure 3B:
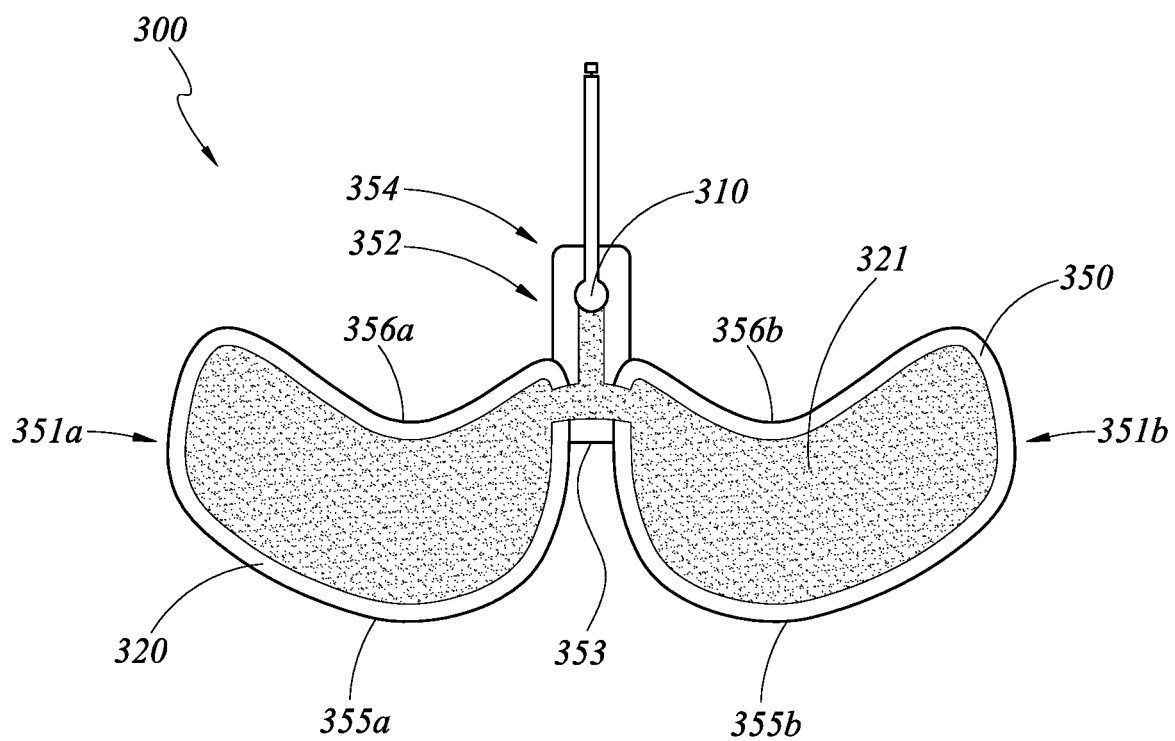
FIG. 3B illustrates an embodiment of a negative pressure wound treatment system employing a wound dressing with a two lobe T shape.

In some embodiments, the wound dressings comprise a specific shape to confirm to an area of the body. The shape of the wound dressing can be tailored to a particular type of wound or a specific surgical incision to be treated. For example, wound dressings can be provided in specific shapes and sizes for application on post-breast surgeries. FIGS. 3A-B illustrate embodiments of wound dressings with shapes that can be used for treatment after breast surgery. FIG. 3A illustrates an embodiment of a wound dressing 300 having a T shape. The T-shaped dressing can include an elongate portion 351, which may be rectangular in shape, and a bridging portion 352, which may also be rectangular in shape. The bridging portion 352 extends upwardly from the middle of the elongate portion 351 to form the T shape. The bridging portion 352 can have a first end 353 where the elongate portion 351 and the bridging portion 352 meet. The elongate portion 351 and bridging portion 352 can form a substantially right angle at the section where the elongate portion 351 and bridging portion 352 meet at the first end 353. The bridging portion 352 can have a second end 354 at the end of the bridging portion 352 that is opposite the first end 353.

In some embodiments, the wound dressing 300 has a length that runs along a longitudinal axis of the elongate portion and a width that runs perpendicular to the length. In some embodiments, the length of the elongate portion 351 is greater than the width of the elongate portion 351. In some embodiments, the length of the bridging portion 352 is less than or equal to the width of the bridging portion 352.

The wound dressing 300 can be a layered dressing similar to the wound dressings described with reference to FIG. 2B. The wound dressing 300 can include wound contact layer (not shown), transmission layer (not shown), an absorbent layer 321, filter (not shown), and a backing layer 320 as described herein. The wound contact layer can be in contact with the wound surface. The transmission layer and absorbent layer 321 can be above the wound contact layer as described herein.

As shown in FIG. 3A, each layer of the T shaped dressing can comprise a T shape. For example, the absorbent layer 321 and underlying transmission layer can be T shaped as illustrated in FIG. 3A. The backing layer 320 and wound contact layer can have the same shape as the absorbent layer and transmission layer but can be larger to provide a perimeter 350 that extends beyond the edge of the absorbent and transmission layer. The backing layer 320 and the wound contact layer can be sealed at the perimeter 350 enclosing the transmission layer and absorbent layer 321 between. For example, the backing layer 320 and wound contact layer can have a T shape with a sealed perimeter 350 that can enclose the T-shaped transmission layer and absorbent layer 321 between.

A fluidic connector or port 310 can be placed over an opening in the backing layer 320 to communicate negative pressure to the wound dressing. The fluidic connector or port 310 is similar to the fluidic connector 110 as described with reference to FIGS. 1A-B and 2A-B herein. The port 310 can be positioned on the bridging portion 352 of the T-shaped wound dressing. As shown in FIG. 3A, the port 310 can be positioned at the second end 354 of the bridging portion 352. The T-shaped dressing can be sized and configured to be used as a dressing for a single breast. In other embodiments, the dressing can be made larger and be sized and configured to be positioned over both breasts with the bridge portion positioned between the breasts. FIG. 3B illustrates an embodiment of a negative pressure wound treatment system employing a wound dressing with a two lobe T shape. The dressing illustrated in FIG. 3B can have a substantially T shape similar to FIG. 3A with an elongated portion 351 and a bridging portion 352 extending upwardly from the middle of the elongate portion forming the T shape. The bridging portion can have a substantially rectangular shape. The lobed T-shaped dressing can have an elongate portion 351 that has two lobes 351a, 351b. The two lobes can have a curved shape as illustrated in FIG. 3B to shape around the breast or other area of the body. The bridging portion 352 can be connected to the two lobes 351a, 351b at a first end 353 of the bridging portion.

The lobed T-shaped wound dressing 300 of FIG. 3B can include a wound contact layer (not shown), a transmission layer (not shown), an absorbent layer 321, filter (not shown), and a backing layer 320 as described herein. The wound contact layer can be in contact with the wound surface. The transmission layer and absorbent layer 321 can be above the wound contact layer as described herein. As shown in FIG. 3B, each layer of the lobed T-shaped dressing can comprise the same shape. For example, the absorbent layer 321 and underlying transmission layer can have the two lobed shape with the bridging portion 352 and the first end 353 as illustrated in FIG. 3B. The backing layer 320 and wound contact layer can have the same shape as the absorbent layer and transmission layer but can be larger to provide a perimeter 350 that extends beyond the edge of the absorbent and transmission layer. The backing layer 320 and the wound contact layer can be sealed at the perimeter 350 enclosing the transmission layer and absorbent layer 321 between. The absorbent layer 321 (and/or the underlying transmission layer) can be a continuous layer between the bridging portion and the elongate portion. For example, the absorbent layer and/or the transmission layer can be one piece of material that is continuous from the port and extend along the bridge portion and can have a narrow portion that extends between the two lobes at the first end 353 as shown in FIG. 3B.

The two lobed wound dressing can have a length that runs along a longitudinal axis of the elongate portion and a width that runs perpendicular to the length. In some embodiments, each lobe 351a and 351b of the elongate portion can have a length that is greater than the width of the lobe. The bridging portion 352 can have a length that is less than or equal to the width. The lobes 351a and 351b can have a lower edge 355a, 355b that is furthest from the port 310. The lower edges 355a, 355b can have a curved shape. In some embodiments the lower edges 355a, 355b can be curved away from the port as shown in FIG. 3B. The lobes 351a and 351b can have as upper edge 356a, 356b that is opposite from the lower edge 355a, 355b. The upper edges 356a, 356b can have the same or substantially the same curvature as the lower edges 355a, 355b.

The bridging portion 352 can include a fluidic connector or port 310 at an opening in the backing layer 320. The fluidic connector or port 310 can be positioned at a second end 354 that is on the opposite end of the bridging portion 352 from the first end 355. The first end 355 communicates negative pressure from the port or fluidic connector 310 through the bridging portion to the two lobes 351a, 351b. The two lobes 351a, 351b of the lobed T-shaped dressing can be used as a single dressing that would cover both breasts. For example, lobe 351a can be used to cover the left breast of the patient while lobe 351b can be used to cover the right breast of the patient. In some embodiments, the single dressing that covers both breasts can have a bra shaped configuration similar to the shaped illustrated in FIG. 3B.

Figure 3C:
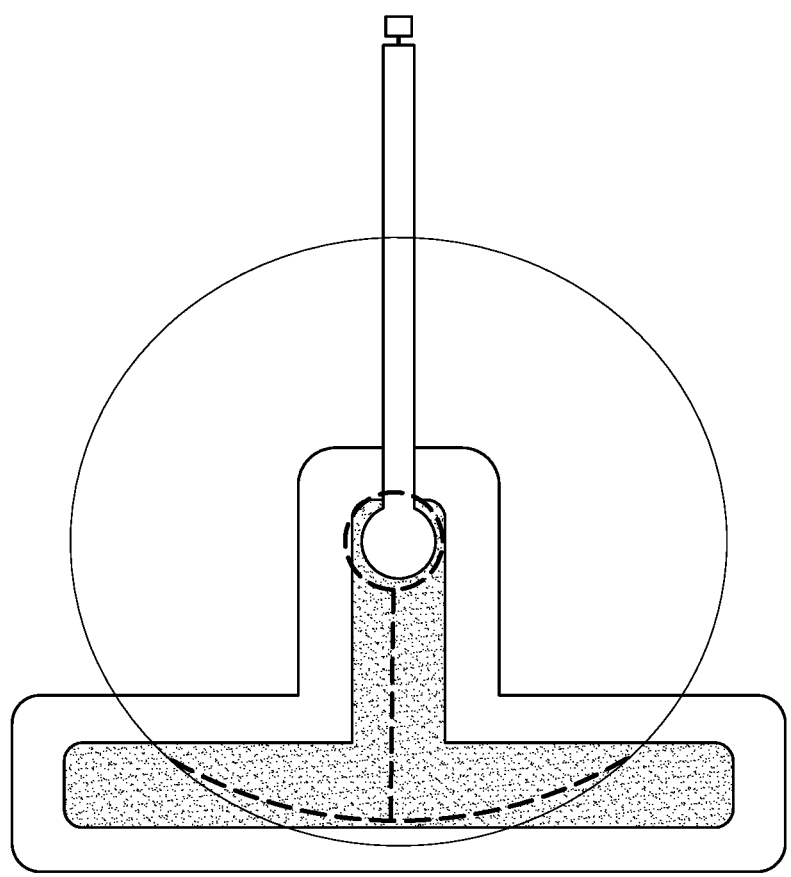
FIG. 3C illustrates an embodiment of a negative pressure wound treatment system employing a wound dressing with a T shape.
Figure 3D:
FIG. 3D illustrates surgical incisions post breast surgery.
Figure 3D:

FIG. 3C illustrates an embodiment of the dressing covering surgical incision sites, illustrated in dashed lines. In some embodiments, the dressing of FIG. 3A includes a T-shape that is arranged to fit the T-shaped incision site for breast surgery. FIG. 3D illustrates an example of a surgical breast procedure and the corresponding incision lines shown post breast surgery. As can be seen in FIG. 3D, the incision can include a T-shaped incision that runs along the lower part of the breast. In some embodiments, this can be similar to an inframammary incision at the lower part of the breast where it meets the chest wall. An additional incision can be perpendicular to the lower section of the breast and extend toward the areola. In some procedures, an incision can be made around the nipple or areola. In some embodiments, this incision can be a periareolar incision. FIG. 3C illustrates surgical incision sites as shown by the dashed lines with relation to the T-shaped dressing of FIG. 3A. The T-shaped dressing can be used to fit over the surgical incision on a single breast. The elongated portion 351 of the dressing can be positioned to cover the incision at the lower section of the breast. The bridging portion 352 of the dressing can be positioned on the incision that extends from the lower section of the breast to the nipple or areola. As shown in FIG. 3C, in some embodiments, the port 310 at the second end 354 of the bridging portion 352 can be positioned on the area of the dressing that is over the incision around the areola.

Figure 3E:
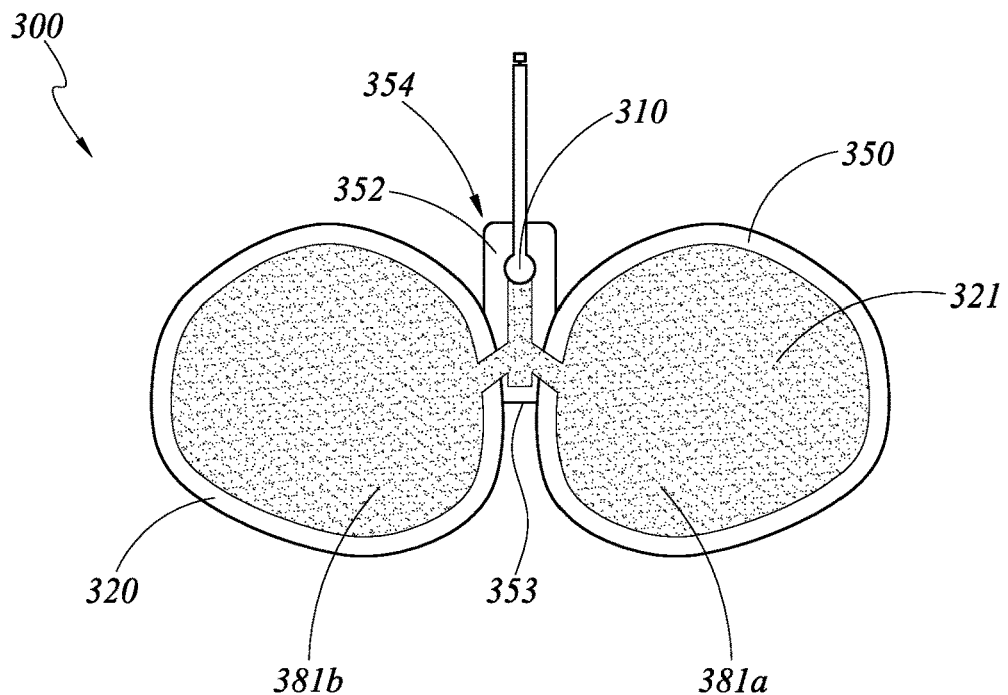
FIG. 3E illustrates an embodiment of a negative pressure wound treatment system employing a wound dressing with a two circular lobe shape.

FIG. 3E illustrates an embodiment of a two lobe wound dressing. The dressing illustrated in FIG. 3E can be bra-shaped similar to FIG. 3B with two lobes, one for each breast and a bridging portion 352 extending upwardly at an intersection between the two lobes. The bridging portion can have a substantially rectangular shape. The lobed bra-shaped dressing can have two lobes 381a, 381b. The two lobes can have a curved shape as illustrated in FIG. 3E to shape around the breast or other area of the body. The bridging portion 352 can be connected to the two lobes 381a, 381b at a first end 353 of the bridging portion located at the intersection between the two lobes. The two lobed wound dressing of FIG. 3E is similar to the two lobed wound dressing of FIG. 3B, however, the two lobed wound dressing of FIG. 3E has two circular or oval shaped lobes. The lobes 381*a*, 381*b* can be circular or oval in shape and can be fluidically connected to each other by a bridging portion 352.

The two lobe wound dressing 300 of FIG. 3E can include a wound contact layer (not shown), a transmission layer (not shown), an absorbent layer 321, filter (not shown), and a backing layer 320 as described herein. The wound contact layer can be in contact with the wound surface. The transmission layer and absorbent layer 321 can be above the wound contact layer as described herein. As shown in FIG. 3E, each layer of the lobed dressing can comprise the same shape. For example, the absorbent layer 321 and underlying transmission layer can have the two lobed shape with the bridging portion 352 and the first end 353 as illustrated in FIG. 3E. The backing layer 320 and wound contact layer can have the same shape as the absorbent layer and transmission layer but can be larger to provide a perimeter 350 that extends beyond the edge of the absorbent and transmission layer. The backing layer 320 and the wound contact layer can be sealed at the perimeter 350 enclosing the transmission layer and absorbent layer 321 between. The absorbent layer 321 (and/or the underlying transmission layer) can be a continuous layer between the bridging portion and the elongate portion. For example, the absorbent layer and/or the transmission layer can be one piece of material that is continuous from the port and extend along the bridge portion and can have a Y-shaped narrow portion that extends between the two lobes at the first end 353 as shown in FIG. 3E.

The bridging portion 352 can include a fluidic connector or port 310 at an opening in the backing layer 320. The fluidic connector or port 310 can be positioned at a second end 354 that is on the opposite end of the bridging portion 352 from the first end 353. The first end 353 communicates negative pressure from the port or fluidic connector 310 through the bridging portion to the two lobes 381*a*, 381*b*. The two lobes 381*a*, 381*b* of the lobed dressing can be used as a single dressing that would cover both breasts. For example, lobe 381*a* can be used to cover the left breast of the patient while lobe 381*b* can be used to cover the right breast of the patient and the bridging portion 352 positioned between the two lobes. In some embodiments, the single dressing that covers both breasts can have the circular shape configuration similar to the shaped illustrated in FIG. 3E.

Figure 3F:
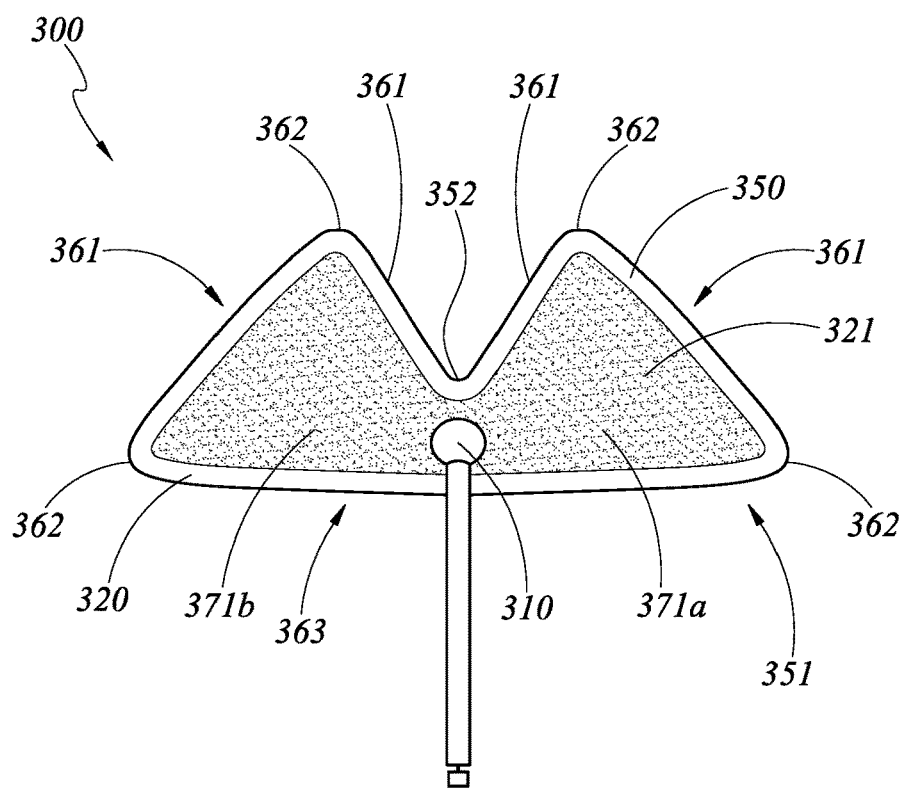
FIG. 3F illustrates an embodiment of a negative pressure wound treatment system employing a wound dressing with a two triangular lobe shape.

FIG. 3F illustrates an embodiment of a triangular shaped dressing that can be one dressing that is used for both breasts. FIG. 3F illustrates an embodiment of a negative pressure wound treatment system employing a wound dressing with a two triangular shaped lobed dressing. The dressing illustrated in FIG. 3F can have two lobes 371*a*, 371*b* with a substantially triangular shape. The dressing can have an elongate portion 351 and a bridging portion 352 in the middle of the elongate portion between the two lobes. The two triangular shaped lobe dressing can have an elongate portion 351 that has two lobes 371*a*, 371*b*. The two lobes can each have a substantially triangular shape as illustrated in FIG. 3F to shape around the surgical incisions of the breast as shown in FIG. 3D or other area of the body. The bridging portion 352 can be connected to the two lobes 371*a*, 371*b* with the first lobe 371*a* on a first side of the bridging portion 352 and a second lobe 371*b* on a second side of the bridging portion 352 as shown in FIG. 3F. FIG. 3F illustrates an embodiment of the wound dressing with the fluid connector 310 extending downward from the elongate portion 351 and away from the middle of the breasts. In some embodiments, the dressing can be positioned over both breasts with the fluidic connector positioned between the breasts as illustrated in FIGS. 3B and 3E.

The triangular shaped lobed wound dressing 300 of FIG. 3F can include a wound contact layer (not shown), a transmission layer (not shown), an absorbent layer 321, filter (not shown), and a backing layer 320 as described herein. The wound contact layer can be in contact with the wound surface. The transmission layer and absorbent layer 321 can be above the wound contact layer as described herein. As shown in FIG. 3F, each layer of the triangular shaped lobe dressing can comprise the same shape. For example, the absorbent layer 321 and underlying transmission layer can have the two lobed shape with the bridging portion 352 as illustrated in FIG. 3F. The backing layer 320 and wound contact layer can have the same shape as the absorbent layer and transmission layer but can be larger to provide a perimeter 350 that extends beyond the edge of the absorbent and transmission layer. The backing layer 320 and the wound contact layer can be sealed at the perimeter 350 enclosing the transmission layer and absorbent layer 321 between. The absorbent layer 321 (and/or the underlying transmission layer) can be a continuous layer between the bridging portion and the elongate portion.

The two triangular shaped lobed wound dressing can have a length that runs along a longitudinal axis of the elongate portion and a width that runs perpendicular to the length. The lobes 371*a* and 371*b* can have edges 361 and corners 362. In some embodiments, each lobe 371*a* and 371*b* of the elongate portion can have a long edge 363 that extends along the longitudinal axis on the lower portion of the dressing. The long edge 363 forms an edge of the first lobe 371*a* and the second lobe 371*b* and a lower portion of the bridging portion 352.

The bridging portion 352 can include a fluidic connector or port 310 at an opening in the backing layer 320. The fluidic connector or port 310 can be positioned at the bridging portion 352 between the two lobes 371*a*, 371*b*. The bridging portion 352 communicates negative pressure from the port or fluidic connector 310 through the bridging portion to the two lobes 371*a*, 371*b*.

As shown in FIG. 3F, the dressing can be positioned over both breasts with the port or fluidic connector 310 positioned on the bridging portion between the breasts. The two triangular shaped portions 371*a*, 371*b* can each cover a single breast. The two lobes 371*a*, 371*b* of the triangular shaped lobed dressing can be used as a single dressing that would cover both breasts. For example, lobe 371*a* can be used to cover the left breast of the patient while lobe 371*b* can be used to cover the right breast of the patient with the bridging portion 352 between the two lobes.

Figure 3G:
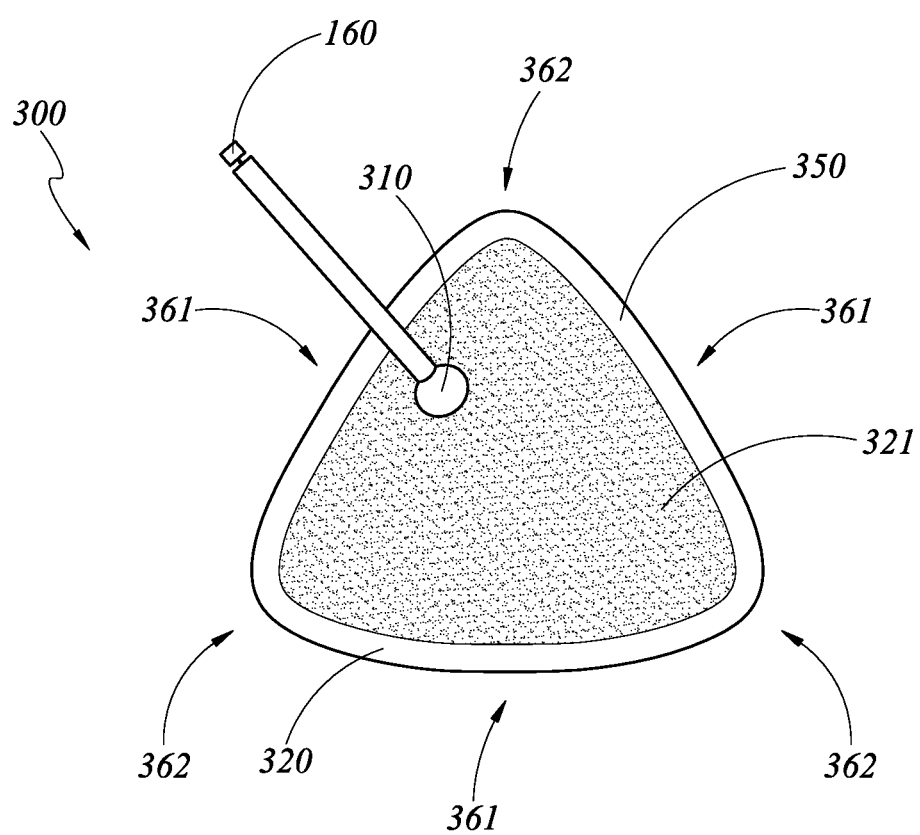
FIG. 3G illustrates an embodiment of a negative pressure wound treatment system employing a wound dressing with a triangular shape.

FIG. 3G illustrates an embodiment of a triangular shaped wound dressing. The wound dressing 300 can be a layered dressing similar to the wound dressings described with reference to FIG. 2B. The triangular shaped dressing can have edges 361 and corners 362. The wound dressing 300 can include wound contact layer (not shown), transmission layer (not shown), an absorbent layer 321, filter (not shown), and a backing layer 320 as described herein. The wound contact layer can be in contact with the wound surface. The transmission layer and absorbent layer 321 can be above the wound contact layer as described herein.

As shown in FIG. 3G, each layer of the triangular shaped dressing can comprise a triangular shape. For example, the absorbent layer 321 and underlying transmission layer can be triangular shaped as illustrated in FIG. 3G. The backing layer 320 and wound contact layer can have the same shape as the absorbent layer and transmission layer but can be larger to provide a perimeter 350 that extends beyond the edge of the absorbent and transmission layer. The backing layer 320 and the wound contact layer can be sealed at the perimeter 350 enclosing the transmission layer and absorbent layer 321 between. For example, the backing layer 320 and wound contact layer can have a triangular shape with a sealed perimeter 350 that can enclose the triangular shaped transmission layer and absorbent layer 321 between.

A fluidic connector or port 310 can be placed over an opening in the backing layer 320 to communicate negative pressure to the wound dressing. The fluidic connector or port 310 is similar to the fluidic connector 110 as described with reference to FIGS. 1A-B and 2A-B herein. As shown in FIG. 3G, the port 310 can be positioned near an edge 361 of the triangular shaped dressing. The triangular shaped dressing can be used as one dressing for each breast. The triangular shaped dressing can be positioned over the T shaped incision similar to the incision shown in FIGS. 3C-3D. In some embodiments, at least one edge 361 of the triangular shaped dressing can be aligned parallel to the incision on the lower portion of the breast. In some embodiments, a corner 362 of the triangular shaped wound dressing can be positioned near the incision around the areola.

Embodiments of the wound dressings, wound dressing components, wound treatment apparatuses and methods described herein may also be used in combination or in addition to those described in International Application No. PCT/GB2014/050781, filed Mar. 14, 2014, published as WO2014/140606A1 on Sep. 18, 2014, titled "WOUND DRESSING AND METHOD OF TREATMENT," the disclosure of which is hereby incorporated by reference in its entirety, including further details relating to the bridging between different portions of the wound dressing which may be applicable to bridging of the absorbent layer and/or transmission layer between the elongate portion and the bridging portion of FIGS. 3A-3C and FIGS. 3E-3G. Additional embodiments of the wound dressings, wound dressing components, wound treatment apparatuses and methods described herein may also be used in combination or in addition to those described in U.S. Publication No. 2014/0350494 A1, the entirety of which is hereby incorporated by reference.

Figure 4A:
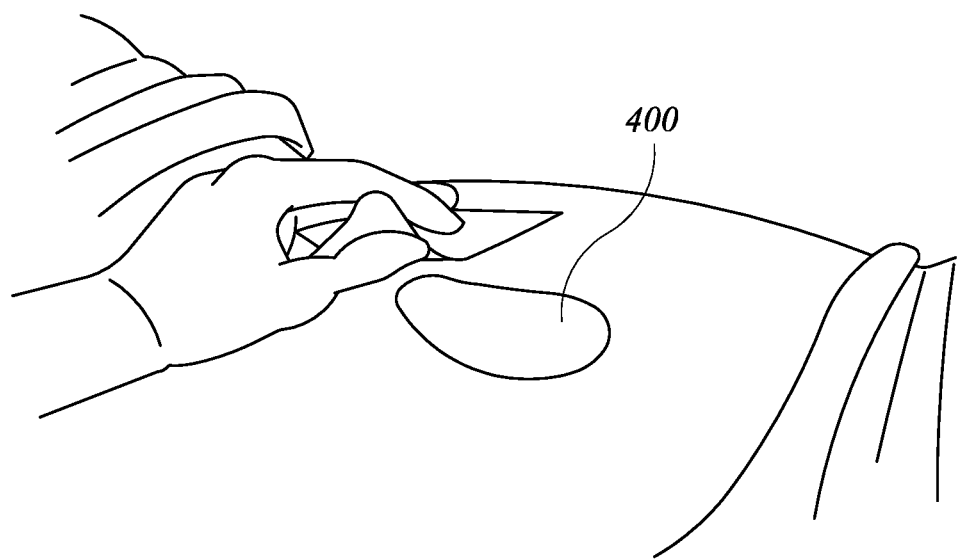
FIGS. 4A-D illustrate the use and application of an embodiment of a wound treatment system onto a patient.

FIGS. 4A-D illustrate the use of an embodiment of a negative pressure therapy wound treatment system being used to treat a wound site on a patient. Although these figures do not illustrate a wound treatment system such as described in FIGS. 3A-3C and FIGS. 3E-3G, it will be appreciated that similar steps may be utilized to treat post-surgical breast wounds. FIG. 4A shows a wound site 400 being cleaned and prepared for treatment. Here, the healthy skin surrounding the wound site 400 is preferably cleaned and excess hair removed or shaved. The wound site 400 may also be irrigated with sterile saline solution if necessary. Optionally, a skin protectant may be applied to the skin surrounding the wound site 400. If necessary, a wound packing material, such as foam or gauze, may be placed in the wound site 400. This may be preferable if the wound site 400 is a deeper wound.

Figure 4B:
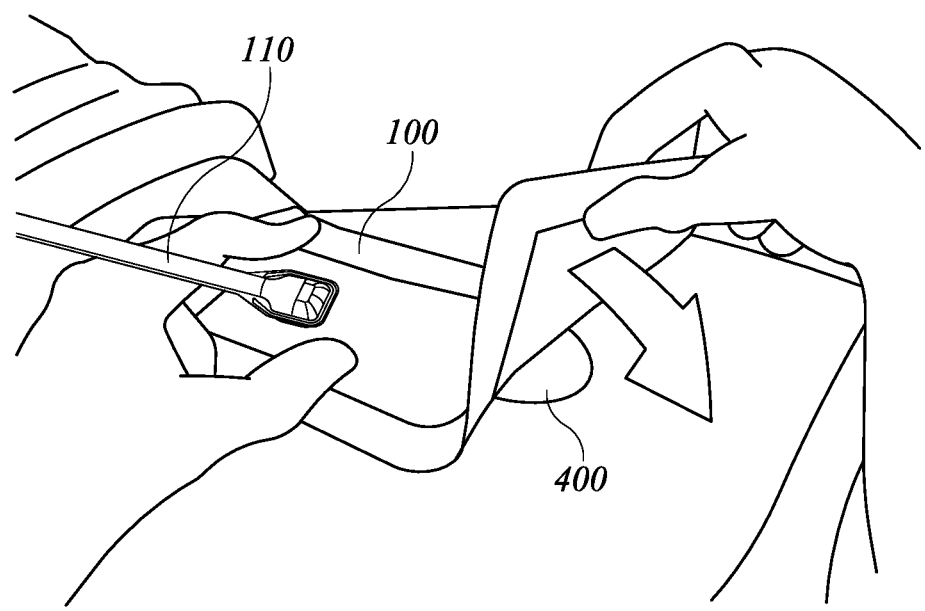

After the skin surrounding the wound site 400 is dry, and with reference now to FIG. 4B, the wound dressing 100 may be positioned and placed over the wound site 400. Preferably, the wound dressing 100 is placed with the wound contact layer over and/or in contact with the wound site 400. In some embodiments, an adhesive layer is provided on the lower surface of the wound contact layer, which may in some cases be protected by an optional release layer to be removed prior to placement of the wound dressing 100 over the wound site 400. Preferably, the dressing 100 is positioned such that the fluidic connector 110 is in a raised position with respect to the remainder of the dressing 10 so as to avoid fluid pooling around the port. In some embodiments, the dressing 100 is positioned so that the fluidic connector 110 is not directly overlying the wound, and is level with or at a higher point than the wound. To help ensure adequate sealing for TNP, the edges of the dressing 100 are preferably smoothed over to avoid creases or folds.

Figure 4C:
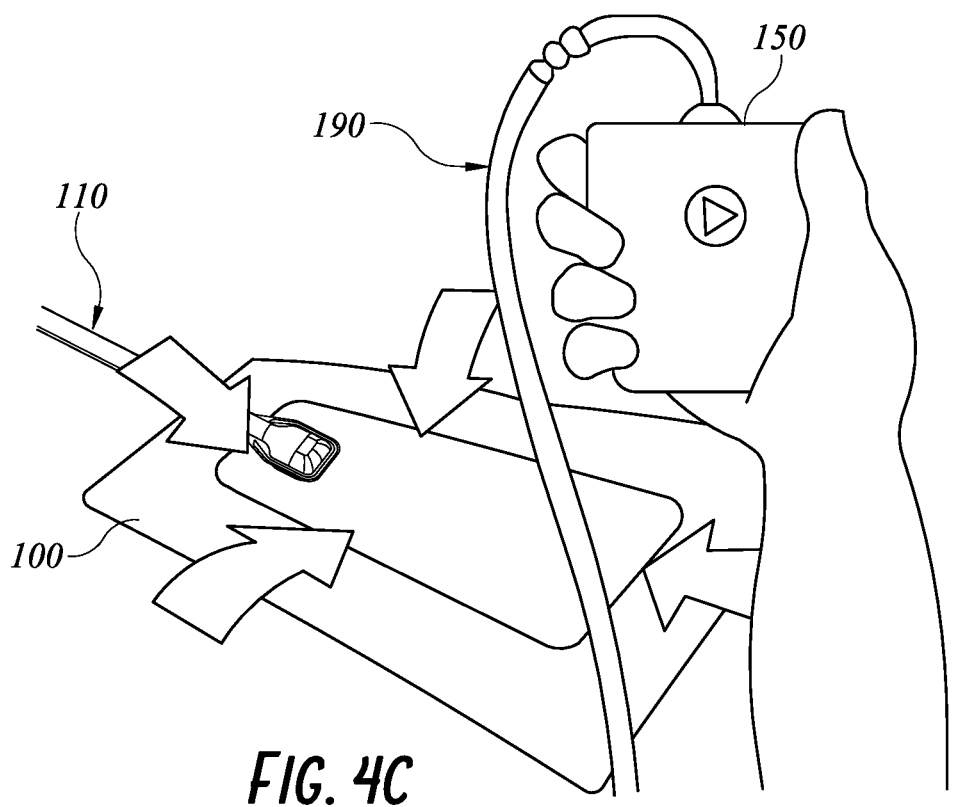

With reference now to FIG. 4C, the dressing 10 is connected to the pump 150. The pump 150 is configured to apply negative pressure to the wound site via the dressing 100, and typically through a conduit. In some embodiments, and as described herein, a fluidic connector 110 may be used to join the conduit 190 from the pump to the dressing 100. Where the fluidic connector is adhered to the top layer of the wound dressing, a length of tubing may be coupled at a first end of the fluidic connector such that the tubing, or conduit, extends away from the fluidic connector parallel to the top of the dressing. In some embodiments the conduit may comprise a fluidic connector. It is expressly contemplated that a conduit may be a soft bridge, a hard tube, or any other apparatus which may serve to transport fluid. Upon the application of negative pressure with the pump 150, the dressing 100 may in some embodiments partially collapse and present a wrinkled appearance as a result of the evacuation of some or all of the air underneath the dressing 100. In some embodiments, the pump 150 may be configured to detect if any leaks are present in the dressing 100, such as at the interface between the dressing 100 and the skin surrounding the wound site 400. Should a leak be found, such leak is preferably remedied prior to continuing treatment.

Figure 4D:
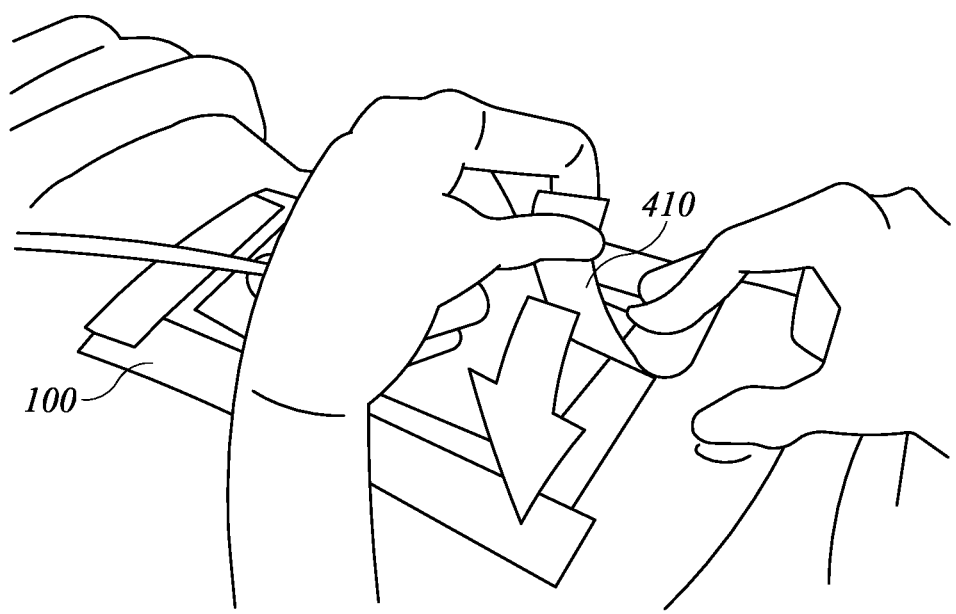

Turning to FIG. 4D, additional fixation strips 410 may also be attached around the edges of the dressing 100. Such fixation strips 410 may be advantageous in some situations so as to provide additional sealing against the skin of the patient surrounding the wound site 400. For example, the fixation strips 410 may provide additional sealing for when a patient is more mobile. In some cases, the fixation strips 410 may be used prior to activation of the pump 150, particularly if the dressing 100 is placed over a difficult to reach or contoured area.

Treatment of the wound site 400 preferably continues until the wound has reached a desired level of healing. In some embodiments, it may be desirable to replace the dressing 100 after a certain time period has elapsed, or if the dressing is full of wound fluids. During such changes, the pump 150 may be kept, with just the dressing 100 being changed.

In some embodiments, one or more wound dressings can be used to treat multiple wound or surgical sites. For example, two of the single breast dressings shown in FIGS. 3A and 3G can be used to treat post-breast surgery sites. As described above one dressing can be placed over the left breast and one dressing can be placed over the right breast. Each of the single breast dressings can include a fluidic connector or port 310 connected to and extending from the dressing as shown in FIGS. 3A and 3G. The fluidic connector or port 310 is similar to the fluidic connector 110 as described with reference to FIGS. 1A-B and 2A-B herein. As described above with reference to FIGS. 3A and 3G, the fluidic connector or port 310 can be positioned on the dressing. The dressing can be T-shaped or triangular as illustrated in FIGS. 3A and 3G, respectively, or can be any other shape utilized for wound dressings including, but not limited to, rectangular, square, or circular dressing shapes. The T-shaped or triangular shaped dressing can be positioned over the T-shaped incision similar to the incision shown in FIGS. 3C-3D as described herein.

When multiple dressings are used to cover the multi-surgery sites, the two or more dressings used in combination can be referred to collectively as a multisite dressing. The multisite dressing can be utilized after a breast surgery as described previously.

FIGS. 3A and 3G illustrate the fluid connector or port 310 extending from the dressing. The multisite dressing can include two dressings used to cover the multiple surgical sites. Each dressing can include a fluid connector or port 310 extending from the dressings for connection to a conduit and/or pump to apply negative pressure to the wound site as described herein. The fluid connector can include a coupling 160 disposed at the proximal end of the fluidic connector. As described with reference to FIGS. 1A-1B, the pump can be connected via a tube to the coupling or can be directly connected to the coupling.

In some embodiments, to minimize the bulk and weight carried by the patient the two fluidic connectors can be connected to a single pump by utilizing a multisite connector. For example, in some embodiments, two dressings can include two fluidic connectors and couplings, one extending from each of the dressings, and the two fluidic connectors can be connected to the single pump with a Y-shaped connector. The Y-shaped connector can be provided in a kit with multisite dressings. In some embodiments, for use in post-breast surgery applications, the Y-shaped connector can be provided in a kit with two dressings, one dressing for each breast, and a pump. In some embodiments, the pump, multi-site dressing, and multisite connector can be used for other surgeries including but not limited to donor site surgeries.

Figure 5A:
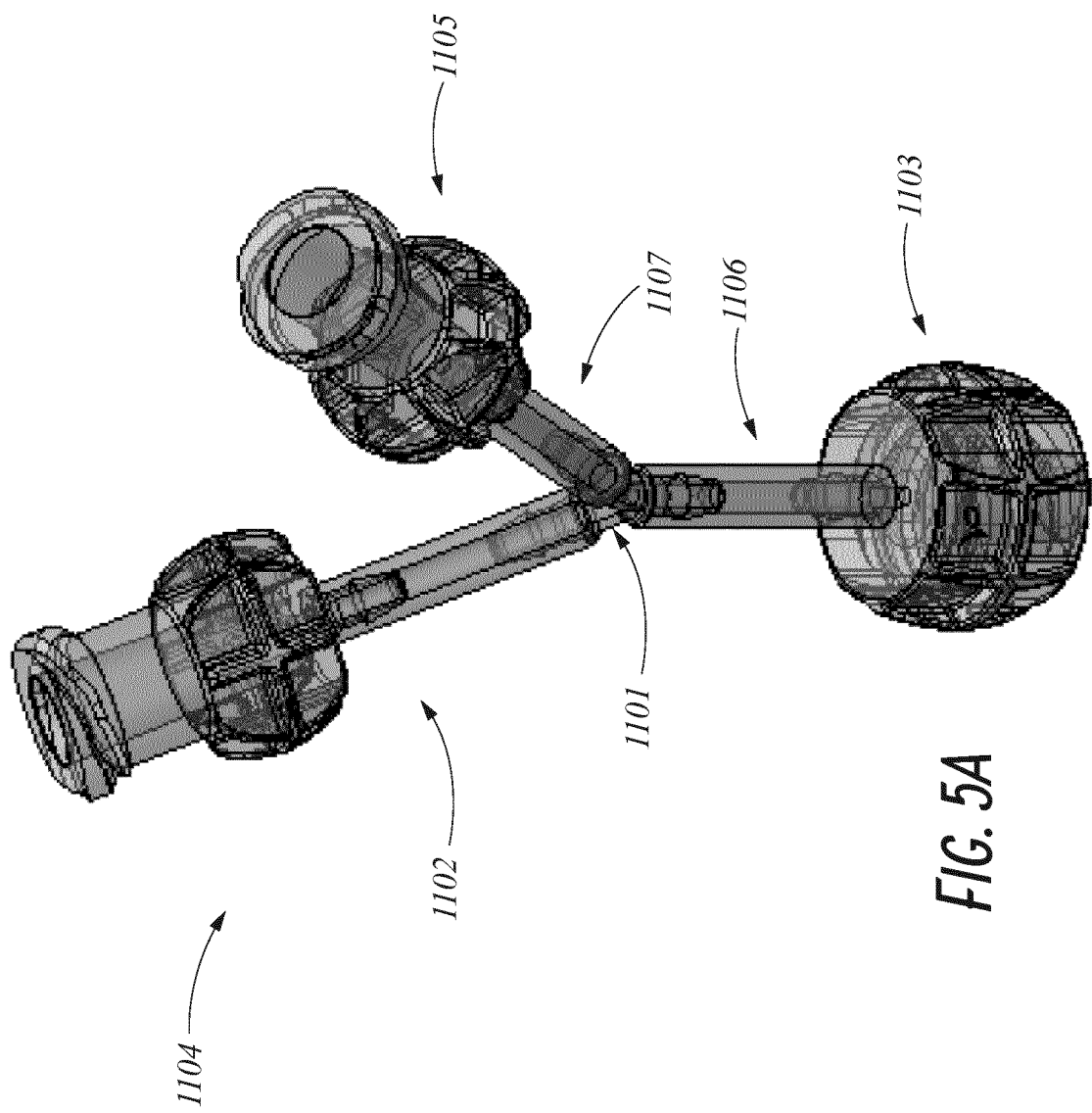
FIGS. 5A and 5B illustrate an embodiment of a Y-shaped connector for a multisite dressing.
Figure 5B:
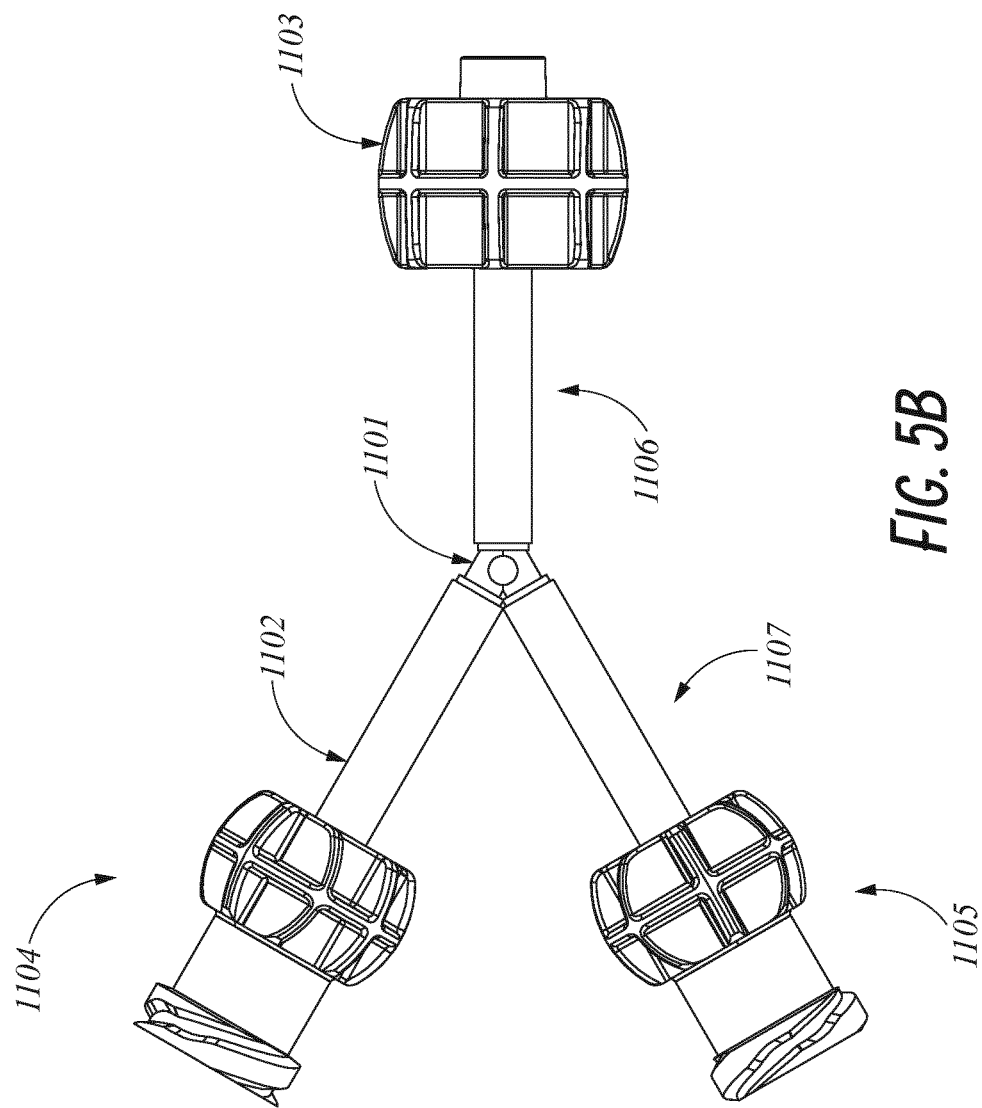

FIGS. 5A and 5B illustrate an embodiment of a Y-shaped connector that can be used with a multisite dressing. The Y-shaped connector can include three conduit attachment portions 1104, 1105, 1103. A pump conduit attachment portion 1103 can be used to connect to a conduit or tubing extending from a pump or to connect to the pump itself. The pump conduit attachment portion 1103 can include a male non-luer connector at a proximal end of the Y-shaped connector. The male connector can attach to a female connector of a conduit or pump. The pump conduit attachment portion 1103 has a shaft 1106 extending from the attachment portion and forming the bottom portion of the Y shape of the connector.

The Y-shaped connector also includes two dressing conduit attachment portions 1104, 1105. The dressing conduit attachment portions 1104, 1105 can be used to connect to the coupling of the fluidic connector extending from a dressing. In some embodiments, a conduit or tubing can be used to connect the fluidic connector to the Y-shaped connector. The conduit or tubing may be a soft bridge, a hard tube, or any other apparatus which may serve to transport fluid. The conduit or tubing can include a coupling at a proximal end and at a distal end. The conduit or tubing can be connected to the coupling of the fluidic connector at the distal end and connected to the conduit attachment portions of the Y-shaped connector at the proximal end of the conduit.

Figure 5C:
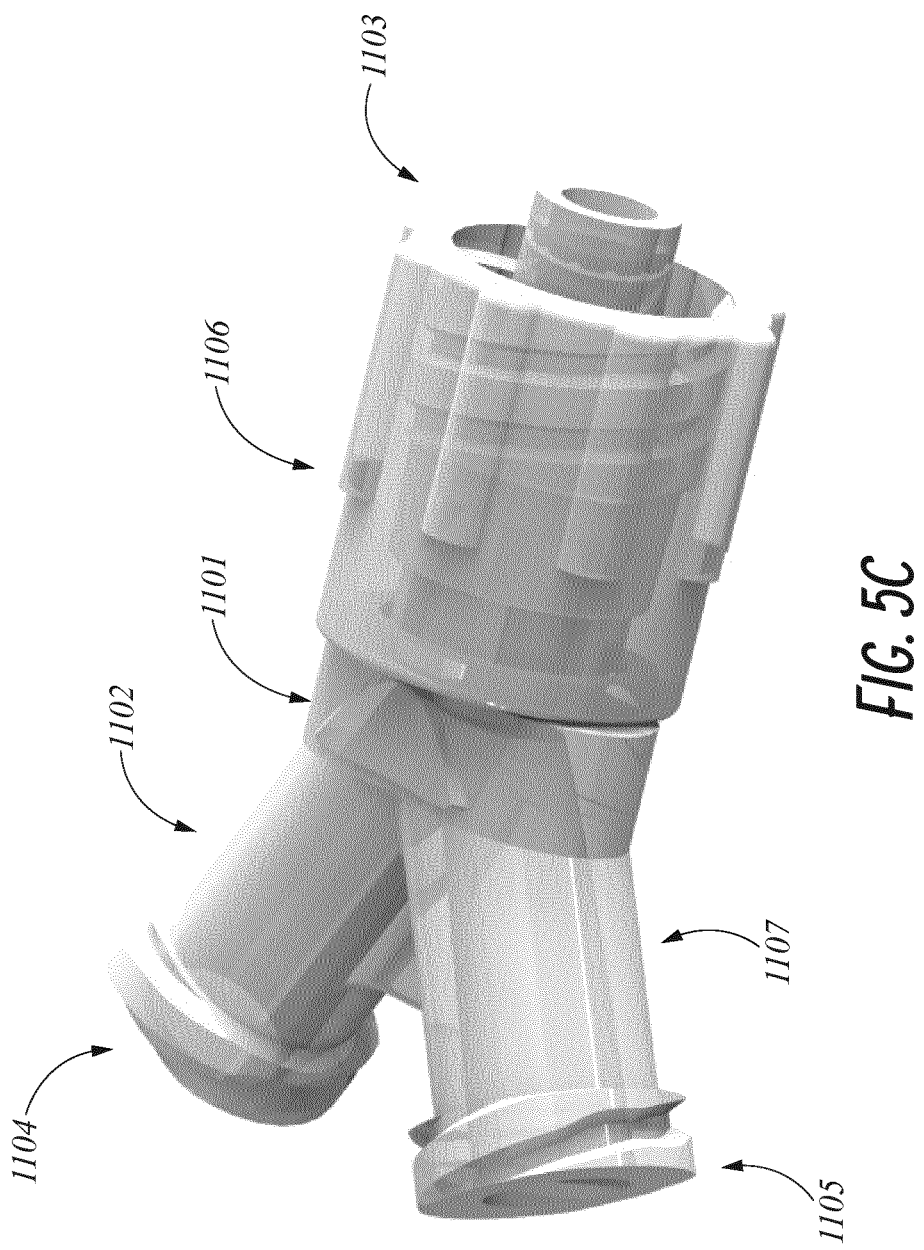
FIG. 5C illustrates an embodiment of a Y-shaped connector that is formed of two parts.

The dressing conduit attachment portion 1104, 1105 can include a female non-luer connector at a distal end of the Y-shaped connector. The female connector can attach to a male connector of the coupling of the fluidic connector or to the coupling of the conduit. In some embodiments, the fluidic connector or the conduit can include a clamp, cap, or other closure mechanism to allow the user to monitor or change one dressing while the other dressing continues to apply negative pressure. In some embodiments the closure mechanism can be a valve, for example, a non-return valve. The dressing conduit attachment portions 1104, 1105 include shafts 1102, 1107, respectively, forming the top portions of the Y shape of the connector as shown in FIGS. 5A-5B. The proximal ends of shafts 1102, 1107 and the distal end of shaft 1106 meet at a joint 1101. In some embodiments, the joint 1101 can include a hinge that allows rotation of the shafts 1102, 1107, 1106 about the joint 1101. In some embodiments, only shafts 1102, 1107 of the dressing conduit attachment portions can more relative to the joint 1101 and the shaft 1106 of the pump conduit attachment portion is fixed. In some embodiments, the whole Y-shaped connector will be in two parts that allow 360° rotation. FIG. 5C illustrates an embodiment of the Y-shaped connector that is formed of two freely-rotating parts that allow rotation of each part relative to the other. The rotation of the Y-shaped connector can allow the user to twist the pump around while the dressings and conduits extending from the dressing remain stationary.

In some embodiments, the male and female non-luer connectors can be a rigid plastic. In some embodiments, the shafts 1106, 1102, 1107 can be a flexible plastic tubing. In some embodiments, the Y-shaped connector can be encased in a soft silicone sleeve to increase patient comfort and prevent the Y-shaped connector from becoming a pressure point.

Utilizing the Y-shaped connector illustrated in FIGS. 5A-5B to attach a single pump to the two dressings, the pump can draw pressure in the two dressings simultaneously. The performance and fluid management of the multisite dressing and Y-connector is equivalent to a control test of the standard single dressing with single pump set-up.

All of the features disclosed in this specification (including any accompanying exhibits, claims, abstract and drawings), and/or all of the steps of any method or process so disclosed, may be combined in any combination, except combinations where at least some of such features and/or steps are mutually exclusive. The disclosure is not restricted to the details of any foregoing embodiments. The disclosure extends to any novel one, or any novel combination, of the features disclosed in this specification (including any accompanying claims, abstract and drawings), or to any novel one, or any novel combination, of the steps of any method or process so disclosed.

Various modifications to the implementations described in this disclosure may be readily apparent to those skilled in the art, and the generic principles defined herein may be applied to other implementations without departing from the spirit or scope of this disclosure. Thus, the disclosure is not intended to be limited to the implementations shown herein, but is to be accorded the widest scope consistent with the principles and features disclosed herein. Certain embodiments of the disclosure are encompassed in the claim set listed below or presented in the future.

What is claimed is:

1. A negative pressure wound therapy apparatus, comprising:
  a wound dressing comprising a triangular shape, the wound dressing having three sides and three corners, the wound dressing comprising:
    a wound contact layer configured to be positioned in contact with a wound, the wound contact layer comprising a first wound facing side and an opposite second side;

an adhesive layer on the first side of the wound contact layer;

an absorbent layer and/or transmission layer positioned over the wound contact layer; and a cover layer configured to cover and form a seal over the wound contact layer and the absorbent layer and/or transmission layer, wherein the cover layer comprises an aperture;

wherein the absorbent layer and/or transmission layer comprise a triangular shape;

wherein the cover layer, the wound contact layer, and the adhesive layer comprise a triangular shape, wherein the cover layer is larger than the absorbent layer and/or the transmission layer to provide a perimeter that extends beyond an edge of the absorbent layer and/or transmission layer, wherein the cover layer and wound contact layer are sealed at the perimeter enclosing the absorbent layer and/or the transmission layer; and wherein the adhesive layer, the wound contact layer, the absorbent layer and/or transmission layer, and the cover layer are configured to be applied to the wound as an integrated unit and wherein the adhesive layer is configured to adhere the triangular shaped wound dressing to the skin around the wound; and a fluidic connector positioned over the aperture in the cover layer.

2. The apparatus of claim 1, wherein the three sides of the wound dressing have a constant curvature along their length.

3. The apparatus of claim 2, wherein the fluidic connector is positioned adjacent to the edge of one of the three sides of the wound dressing.

4. The apparatus of claim 1, wherein the fluidic connector is configured to communicate negative pressure to the wound dressing.

5. The apparatus of claim 1, further comprising a Y-connector configured to provide fluid communication between the wound dressing and fluidic connector and a second wound dressing and second fluidic connector and a negative pressure source.

6. The apparatus of claim 1, wherein the dressing is sized and configured to cover one or more post-surgical breast wounds, wherein at least one of the sides of the triangular shaped dressing is configured to be aligned parallel to an incision on a lower portion of the breast and a corner of the triangular shaped wound dressing is configured to be positioned over an incision around an areola of a patient.

7. The apparatus of claim 1, wherein the wound contact layer, absorbent layer and/or transmission layer, and cover layer are configured to extend over skin surrounding the wound.

* * * * *